(12) United States Patent
Lynn

(10) Patent No.: US 9,174,845 B2
(45) Date of Patent: Nov. 3, 2015

(54) OZONATED LIQUID DISPENSING UNIT

(75) Inventor: Daniel W. Lynn, Omaha, NE (US)

(73) Assignee: Food Safety Technology, LLC, Omaha, NE (US)

( * ) Notice: Subject to any disclaimer, the term of this patent is extended or adjusted under 35 U.S.C. 154(b) by 176 days.

(21) Appl. No.: 12/816,837

(22) Filed: Jun. 16, 2010

(65) Prior Publication Data

US 2010/0252415 A1    Oct. 7, 2010

Related U.S. Application Data

(63) Continuation-in-part of application No. 12/179,335, filed on Jul. 24, 2008.

(51) Int. Cl.
*C01B 13/11* (2006.01)
*A23B 7/157* (2006.01)
(Continued)

(52) U.S. Cl.
CPC ............. *C01B 13/11* (2013.01); *A23B 7/157* (2013.01); *A23B 7/158* (2013.01); *A61L 2/183* (2013.01);
(Continued)

(58) Field of Classification Search
CPC ........ C01B 13/11; A23B 7/157; A23B 7/158; A61L 2/18; A61L 2/183; C11D 3/36; C11D 3/50; B01F 3/04744; B01F 3/04836
USPC ...................... 422/255, 256, 28, 29
See application file for complete search history.

(56) References Cited

U.S. PATENT DOCUMENTS 3,298,314 A    1/1967   Kopczynski
3,549,134 A    12/1970  Kapacheva et al.
(Continued)

FOREIGN PATENT DOCUMENTS

CA    2491781    7/2005
DE    202 0050 11195 U1    1/2006
(Continued)

OTHER PUBLICATIONS

Office Action for U.S. Appl. No. 12/179,335 dated Nov. 23, 2011 (12 pages).
(Continued)

*Primary Examiner* — Regina M Yoo
(74) *Attorney, Agent, or Firm* — Polsinelli PC

(57) ABSTRACT

A ozonated liquid dispensing unit is described. The unit produces and dispenses an ozonated liquid that may be used to clean and sanitize a variety of articles or used in conjunction with cleaning processes and other apparatus. The unit includes a liquid input port to receive liquid into the unit. The unit includes a first dielectric cell for producing ozone gas from ambient air and a second dielectric cell for producing ozone gas. The first dielectric cell is in supply communication with the second dielectric cell for supplying the second dielectric cell with a supply gas containing the ozone gas generated from the ambient air. The second dielectric cell produces ozone gas from the supply gas. An injector is in fluidic communication with the liquid input port. The injector in supply communication with the second dielectric cell for receiving the ozone gas from the second dielectric cell, and the injector mixes the ozone gas from the second dielectric cell with the liquid from the liquid input port to produce an ozonated liquid. A liquid output port discharges the ozonated liquid from the unit. A faucet or spray may be used to control the discharge of the ozonated liquid from the unit.

27 Claims, 11 Drawing Sheets

(51) Int. Cl.

| | | |
|---|---|---|
| *A23B 7/158* | (2006.01) | |
| *C11D 3/39* | (2006.01) | |
| *C11D 3/50* | (2006.01) | |
| *B01F 3/04* | (2006.01) | |
| *A61L 2/18* | (2006.01) | |

(52) U.S. Cl.
CPC ......... *B01F 3/04744* (2013.01); *B01F 3/04836* (2013.01); *C11D 3/39* (2013.01); *C11D 3/50* (2013.01); *A23V 2002/00* (2013.01); *A61L 2/18* (2013.01); *B01F 2003/04886* (2013.01); *C01B 2201/32* (2013.01); *C01B 2201/40* (2013.01); *C01B 2201/62* (2013.01); *C01B 2201/64* (2013.01)

(56) References Cited

U.S. PATENT DOCUMENTS

| | | | |
|---|---|---|---|
| 4,035,657 A | 7/1977 | Carlson | |
| 4,049,552 A | 9/1977 | Arff | |
| 4,123,800 A | 10/1978 | Mazzei | |
| 4,138,330 A | 2/1979 | Garrett | |
| 4,176,061 A | 11/1979 | Stopka | |
| 4,352,740 A | 10/1982 | Grader et al. | |
| 4,517,159 A | 5/1985 | Karlson | |
| 4,555,335 A | 11/1985 | Burris | |
| 4,650,573 A | 3/1987 | Nathanson | |
| 4,686,036 A | 8/1987 | Laederach-Zaugg | |
| 4,801,310 A | 1/1989 | Bielefeldt | |
| 4,834,343 A | 5/1989 | Boyes | |
| 4,849,237 A | 7/1989 | Hurst | |
| 4,900,481 A | 2/1990 | Kishioka | |
| 4,963,269 A | 10/1990 | Sasaki et al. | |
| 5,005,364 A * | 4/1991 | Nelson | 62/76 |
| 5,009,816 A * | 4/1991 | Weise et al. | 261/21 |
| 5,069,880 A | 12/1991 | Karlson | |
| 5,174,905 A | 12/1992 | Shaw | |
| 5,186,841 A | 2/1993 | Schick | |
| 5,207,237 A | 5/1993 | Langford | |
| 5,213,773 A | 5/1993 | Burris | |
| 5,236,512 A | 8/1993 | Rogers et al. | |
| 5,411,713 A | 5/1995 | Iwanaga | |
| 5,493,754 A | 2/1996 | Gurstein et al. | |
| 5,514,267 A | 5/1996 | Machiya | |
| 5,556,200 A | 9/1996 | Ekholm et al. | |
| 5,641,456 A | 6/1997 | Rosenauer | |
| 5,645,797 A | 7/1997 | Lo | |
| 5,670,094 A | 9/1997 | Sasaki et al. | |
| 5,720,905 A | 2/1998 | Ho | |
| 5,815,869 A | 10/1998 | Hopkins | |
| 5,824,243 A * | 10/1998 | Contreras | 261/36.1 |
| 5,824,274 A * | 10/1998 | Long | 708/140 |
| 5,839,155 A | 11/1998 | Berglund et al. | |
| 5,855,856 A | 1/1999 | Karlson | |
| 5,863,128 A | 1/1999 | Mazzei | |
| 5,865,995 A | 2/1999 | Nelson | |
| 5,914,089 A | 6/1999 | Murakami et al. | |
| 5,951,511 A * | 9/1999 | Lowder | 604/73 |
| 5,951,921 A | 9/1999 | Koganezawa et al. | |
| 6,030,586 A | 2/2000 | Kuan | |
| 6,039,815 A | 3/2000 | Yeol et al. | |
| 6,076,808 A | 6/2000 | Porter | |
| 6,106,731 A | 8/2000 | Hayes | |
| 6,115,862 A | 9/2000 | Cooper et al. | |
| 6,132,629 A | 10/2000 | Boley | |
| 6,153,151 A | 11/2000 | Moxley et al. | |
| 6,197,206 B1 | 3/2001 | Wasinger | |
| 6,200,014 B1 | 3/2001 | Babenko | |
| 6,207,064 B1 | 3/2001 | Gargas | |
| 6,250,324 B1 | 6/2001 | Conrad et al. | |
| 6,254,838 B1 | 7/2001 | Goede | |
| 6,274,053 B1 | 8/2001 | Conrad | |
| 6,276,304 B1 | 8/2001 | Tai | |
| 6,315,887 B1 | 11/2001 | Salama | |
| 6,348,227 B1 | 2/2002 | Caracciolo | |
| 6,361,688 B1 | 3/2002 | Nelson | |
| 6,402,855 B1 * | 6/2002 | Damron et al. | 134/10 |
| 6,455,017 B1 * | 9/2002 | Kasting et al. | 422/292 |
| 6,458,257 B1 | 10/2002 | Andrews et al. | |
| 6,458,398 B1 | 10/2002 | Smith et al. | |
| 6,464,210 B1 | 10/2002 | Teran et al. | |
| 6,485,769 B2 * | 11/2002 | Audy et al. | 426/320 |
| 6,499,671 B1 | 12/2002 | Sands et al. | |
| 6,517,731 B2 | 2/2003 | Conrad | |
| 6,585,898 B1 | 7/2003 | Ekberg et al. | |
| 6,638,364 B2 | 10/2003 | Harkins et al. | |
| 6,649,052 B2 | 11/2003 | Lee et al. | |
| 6,755,977 B2 | 6/2004 | Brunsell | |
| 6,808,637 B2 | 10/2004 | Cho | |
| 6,817,541 B2 | 11/2004 | Sands et al. | |
| 6,837,944 B2 * | 1/2005 | Kashkoush et al. | 134/28 |
| 6,886,373 B2 * | 5/2005 | Carrubba et al. | 68/222 |
| 6,948,504 B2 | 9/2005 | Fittkau et al. | |
| 6,962,654 B2 | 11/2005 | Arnaud | |
| 6,964,739 B2 | 11/2005 | Boyd et al. | |
| 6,982,006 B1 * | 1/2006 | Boyers et al. | 134/3 |
| 6,991,685 B2 | 1/2006 | Kravitz et al. | |
| 7,022,225 B1 | 4/2006 | Clawson et al. | |
| 7,086,407 B2 | 8/2006 | Lynn | |
| 7,087,123 B2 | 8/2006 | Lynn | |
| 7,087,124 B2 | 8/2006 | Lynn | |
| 7,108,781 B2 | 9/2006 | Martin | |
| 7,188,632 B2 | 3/2007 | Lynn | |
| 7,255,332 B2 | 8/2007 | Osborn et al. | |
| 7,264,006 B2 | 9/2007 | Fittkau et al. | |
| 7,264,680 B2 | 9/2007 | Gebhart et al. | |
| 7,272,947 B2 | 9/2007 | Anderson et al. | |
| 7,275,982 B1 | 10/2007 | Brandt et al. | |
| 7,276,168 B2 | 10/2007 | Haibara et al. | |
| 7,425,301 B2 | 9/2008 | Gillette et al. | |
| 8,071,526 B2 | 12/2011 | Lynn | |
| 2002/0190404 A1 | 12/2002 | Baarda | |
| 2003/0049164 A1 | 3/2003 | Bon et al. | |
| 2003/0156978 A1 * | 8/2003 | Gillette et al. | 422/31 |
| 2004/0074252 A1 * | 4/2004 | Shelton | 62/318 |
| 2004/0154641 A1 | 8/2004 | Montierth | |
| 2005/0103725 A1 | 5/2005 | Palm et al. | |
| 2005/0167369 A1 | 8/2005 | Robinson et al. | |
| 2005/0214159 A1 | 9/2005 | Schwei et al. | |
| 2006/0102193 A1 * | 5/2006 | Lyubchik et al. | 134/1 |
| 2006/0175263 A1 | 8/2006 | Rice et al. | |
| 2007/0086913 A1 * | 4/2007 | Teran et al. | 422/28 |
| 2007/0199581 A1 | 8/2007 | Lynn et al. | |
| 2007/0205161 A1 | 9/2007 | Chiba et al. | |
| 2008/0227680 A1 | 9/2008 | Lynn | |
| 2009/0008806 A1 | 1/2009 | Lynn | |
| 2009/0032473 A1 | 2/2009 | Ueki et al. | |
| 2009/0120473 A1 | 5/2009 | Lynn | |
| 2009/0233839 A1 | 9/2009 | Lynn | |
| 2010/0010422 A1 | 1/2010 | Watanabe | |
| 2010/0021598 A1 | 1/2010 | Lynn | |
| 2010/0252415 A1 | 10/2010 | Lynn | |

FOREIGN PATENT DOCUMENTS

| | | |
|---|---|---|
| GB | 2 144 610 | 3/1985 |
| JP | 52-125466 A | 10/1977 |
| JP | H06-039232 A | 2/1994 |
| JP | 2003-320232 A | 11/2003 |
| JP | 2004-066050 A | 3/2004 |
| JP | 2004-330050 A | 11/2004 |
| JP | 2005-021869 A | 1/2005 |
| JP | 2005-144320 A | 6/2005 |
| JP | 2005-334797 A | 12/2005 |
| JP | 2008-012415 A | 1/2008 |
| JP | 2008-524530 A | 7/2008 |
| JP | 2009-142750 A | 9/2008 |
| JP | 2009-274026 A | 11/2009 |
| JP | H10-034173 A | 2/2010 |
| RU | 2 177 456 C2 | 1/2000 |
| SU | 1049091 A | 10/1983 |
| WO | 01-72432 A1 | 10/2001 |

(56) References Cited

FOREIGN PATENT DOCUMENTS

| WO | 03-084652 A2 | 10/2003 |
| WO | 2008-112947 A1 | 9/2008 |
| WO | 2010-047167 A | 4/2010 |

OTHER PUBLICATIONS

International Search Report and Written Opinion dated Dec. 2, 2011 for PCT/US2011/039756 (11 pages).
International Search Report and Written Opinion dated Sep. 1, 2009 for PCT/US09/51636 (7 pages).
Office Action for U.S. Appl. No. 12/179,335 dated Jun. 7, 2012 (11 pages).
Office Action for U.S. Appl. No. 12/179,335 dated Sep. 26, 2013 (13 pages).
Office Action for U.S. Appl. No. 12/179,335 dated May 16, 2014 (11 pages).
AU Appl. No. 2011267991 Examination Report dated Jun. 7, 2013 (4 pages).
Office Action for U.S. Appl. No. 12/468,952 dated Nov. 25, 2011 (17 pages).
Office Action for U.S. Appl. No. 12/468,952 dated May 9, 2013 (6 pages).
Office Action for U.S. Appl. No. 12/047,498 dated Aug. 31, 2010 (13 pages).
Office Action for U.S. Appl. No. 12/047,461 dated May 21, 2010 (12 pages).
Office Action for U.S. Appl. No. 12/047,442 dated May 12, 2010 (15 pages).
Office Action for U.S. Appl. No. 12/047,442 dated Jan. 10, 2011 (20 pages).
Office Action for U.S. Appl. No. 12/047,442 dated Dec. 16, 2013 (24 pages).
Office Action for U.S. Appl. No. 12/047,442 dated Oct. 16, 2014 (24 pages).
International Search Report and Written Opinion dated Oct. 5, 2011 for PCT/US2011/039711 (9 pages).
International Search Report and Written Opinion dated Jun. 3, 2008 for PCT/US08/56936 (13 pages).
SUSLOW; "Oxidation Reduction Potential (ORP) for Water Disinfection Monitoring, Control and Documentation"; University of California, Division of Agriculture and Natural Resources, 2004 (5 pages).

* cited by examiner

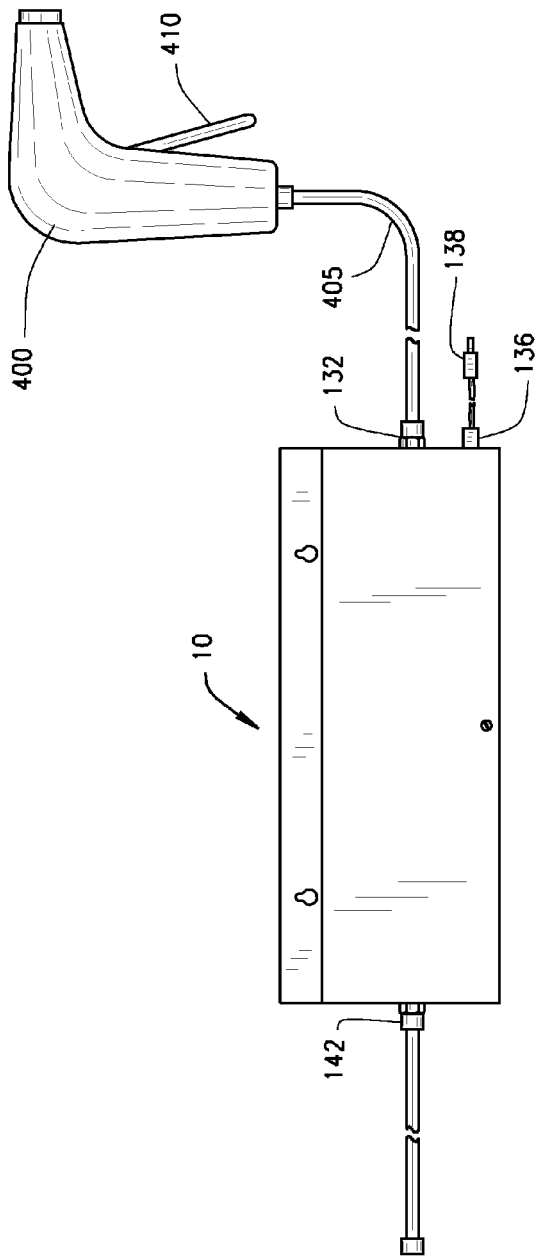
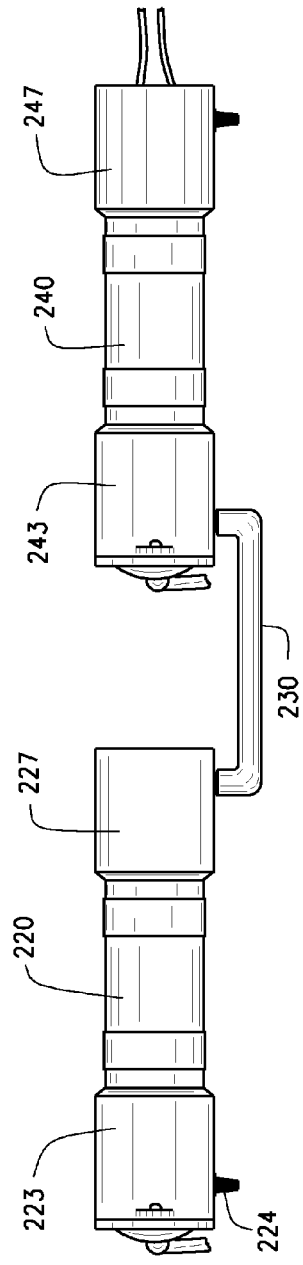

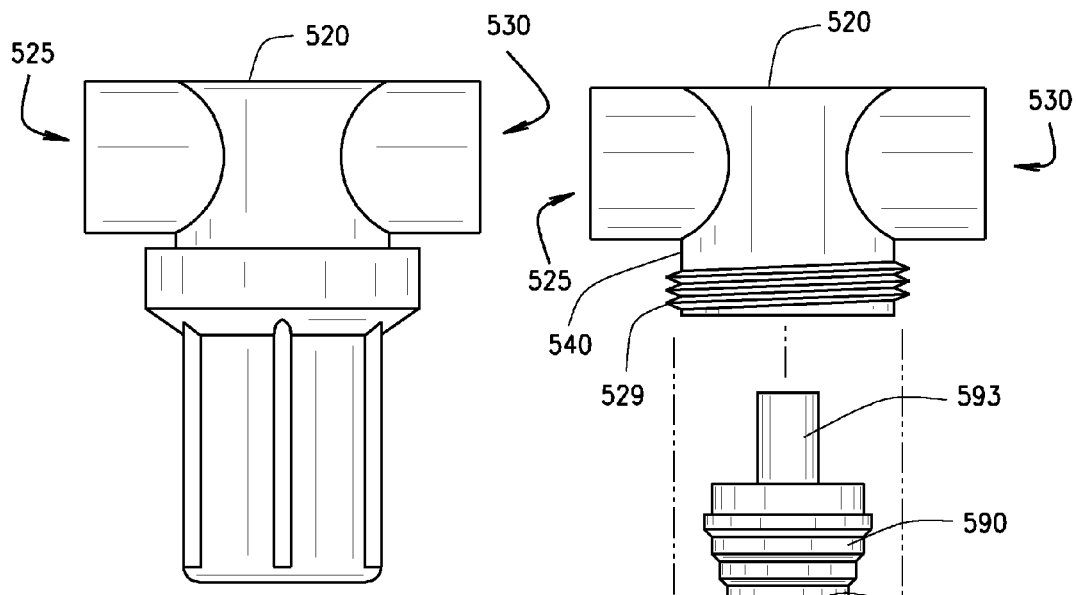
FIG. 9
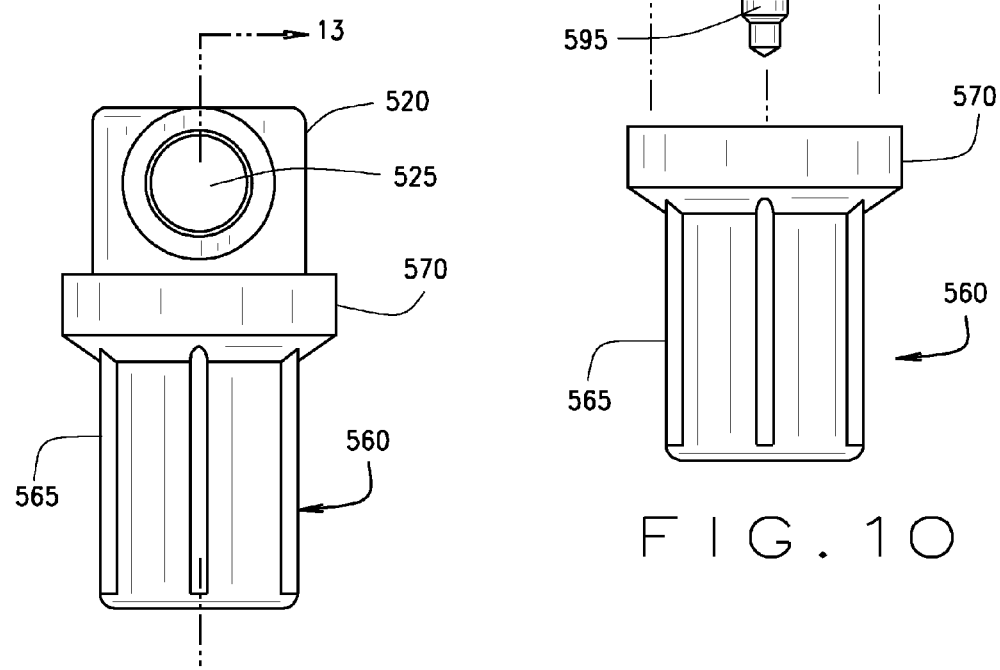
FIG. 10
FIG. 11

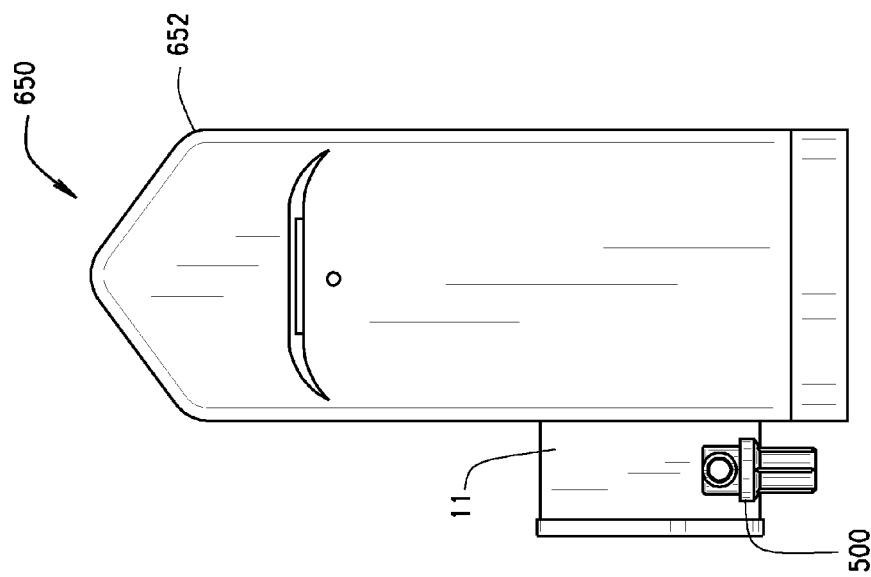
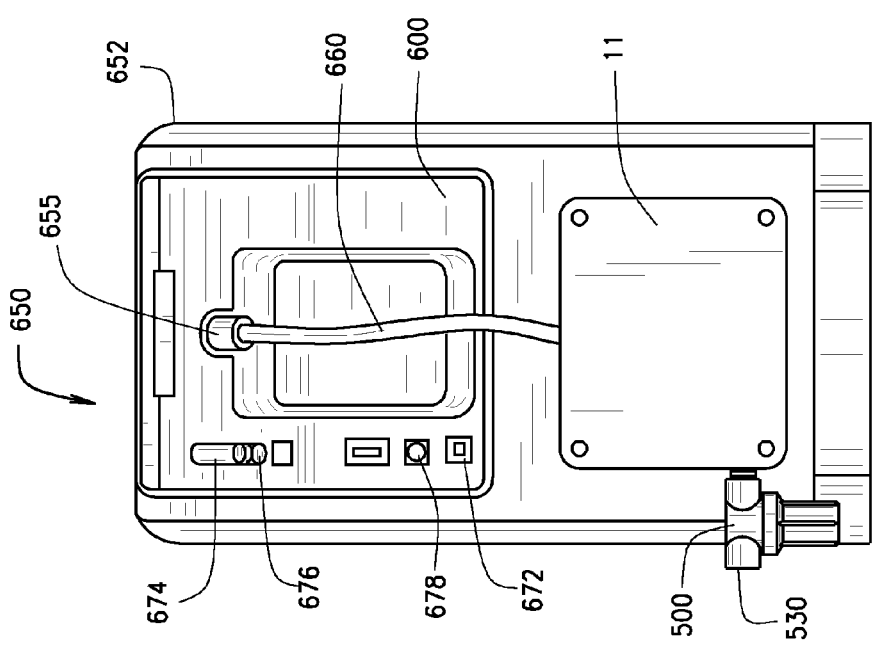

OZONATED LIQUID DISPENSING UNIT

CROSS REFERENCE TO RELATED APPLICATION

This application is a continuation-in-part of U.S. Nonprovisional patent application Ser. No. 12/179,335 filed Jul. 24, 2008, which is hereby incorporated by reference.

FIELD OF INVENTION

The present invention relates to an ozonated liquid dispensing unit that produces and dispenses an ozonated liquid that may be used to clean and sanitize a variety of articles or used in conjunction with cleaning processes and other apparatus.

BACKGROUND OF INVENTION

Prior attempts to provide an ozonated liquid in a kitchen environment have failed to provide an ozonated liquid with sufficient concentrations of ozone resulting in poor cleaning and sanitizing. Without sufficient ozone concentration, conventional cleaning and sanitizing methods may still be necessary at extra labor, equipment, and supply costs.

Other prior attempts to provide an ozonated liquid have involved electrochemical ozone generation. Such systems are difficult to maintain. Such systems are often too large and too bulky to be effectively used in some residential or commercial applications. Many of these systems are also too expensive for use in the home or are not economical to be used in commercial applications. Such systems often require significant mechanical alterations to existing water supply and delivery systems. Such systems also require the output of ozone gas to be adjusted each time the system is turned on. Further, many previous systems cannot be used with multiple, different dispensing applications.

Other prior attempts to provide an ozonated liquid have involved systems that create too much off-gassing of ozone. Although ozone gas is generally harmless, OSHA workplace requirements require that ozone levels are maintained below certain minimums.

SUMMARY OF INVENTION

An ozonated liquid dispensing unit is described herein. The unit produces and dispenses an ozonated liquid that may be used to clean and sanitize a variety of articles or used in conjunction with cleaning processes and other apparatus. The unit is compact, may be conveniently installed in a commercial or residential kitchen, restroom or other area with a water supply. The units provides an ozonated liquid with a high concentration of ozone gas sufficient to clean and sanitize food items, food preparation items, food preparation surface, bathrooms, medical equipment, drains and to provide for hand-washing and hygiene needs. The unit uses multiple dielectric cells in an in-line configuration to create the ozone gas that is mixed with the water to form the ozonated liquid. A first dielectric cell prepares ozone gas that is supplied to a second dielectric cell, which creates additional ozone gas, thus creating a highly concentrated supply of ozone gas that is supplied to an injector.

Foods, food preparation areas as well as other surfaces that may benefit from sterilization provided by the unit. In the food industry, the ozonated liquid from the unit provides for chemical-free sterilization of contaminated surfaces and tools, such as those used in the processing of raw meat. The ozonated liquid cleans toxic substances 3,000 times faster than chlorine, and unlike chlorine, ozonated liquid is completely safe and natural. The ozonated liquid kills microorganisms, including *E. coli*, salmonella, bacteria, viruses, molds, etc. The ozonated liquid also remove pesticides and other residues from fruits and vegetables. The ozonated liquid also reduces odors in the environment on which the ozonated liquid is sprayed. The unit is ideal for residential food preparation, commercial food preparation, or any place a sterile, cleaning solution is needed. In a commercial setting, fruits and vegetables may be washed with the unit and its ozonated liquid to increase the shelf-life of the items. By removing the micro-organisms from the surfaces of the fruit and vegetables that may cause decay and spoilage, the fruit and vegetables will not decay or spoil as fast.

The ozonated liquid dispensing unit includes a liquid input port to receive the liquid, such as water, into the unit to be mixed with ozone gas to form the ozonated liquid. The unit includes the first dielectric cell for producing ozone gas from ambient air and the second dielectric cell for producing ozone gas. The first dielectric cell is in supply communication with the second dielectric cell for supplying the second dielectric cell with a supply gas comprising the ozone gas generated from the ambient air. The second dielectric cell produces ozone gas from the supply gas. The injector is in fluidic communication with the liquid input port. The injector in supply communication with the second dielectric cell for receiving the ozone gas from the second dielectric cell, and the injector mixes the ozone gas from the second dielectric cell with the liquid from the liquid input port to produce an ozonated liquid. A liquid output port discharges the ozonated liquid from the unit. A faucet or spray may be used to control the discharge of the ozonated liquid from the unit.

The unit is easy to install. Generally, the unit is just plugged into an electrical unit and a water supply is provided to the unit. The unit discharges the ozonated liquid into a liquid supply line in fluidic communication with a sprayer or faucet. A handle, knob or other actuator is manipulated in order to begin the production and flow of ozonated liquid from the unit.

Ozone gas is unstable, which provides for it cleaning and sanitizing capabilities, but also makes consistent ozone levels difficult to maintain when the gas is mixed into a solution. Ozone gas cannot be packaged or stored and must be generated on site. The unit reduces the need for chemicals, hot water, and labor. Conventional cleaning systems often require the use of warm or hot water, which may form condensation in the surrounding workspace. This condensation may provide for or encourage the growth of microorganisms. Because unit only uses cold water, condensation is less likely to form in the surrounding workspace. The unit also reduces the hydraulic load on the waste-water treatment system and eliminates the need to treat the chemicals that would be present in conventional wastewater discharge streams.

Ozone creates none of the trihalomethanes commonly associated with chlorine compounds. When properly matched to the application, ozone will reduce most organic compounds to carbon dioxide, water and a little heat. Finally, as ozone sheds the atom of the oxygen causing its molecular instability during the oxidation process, it becomes oxygen again.

In other aspects, an ozonated liquid dispensing unit is provided that receives oxygen gas from an oxygen concentrator. The unit uses multiple dielectric cells in an in-line configuration to create ozone gas from the oxygen gas. The ozone gas is injected into water or fluid to form the ozonated liquid.

In other aspects, a reaction vessel for processing an ozonated fluid is provided. The reaction vessel includes an assembly, which includes a fluid entry opening to receive an ozonated fluid and a fluid exit opening to discharge the ozonated fluid. The reaction vessel further includes a container, and the assembly engages the container. The container holds a core. The container is in fluidic communication with the fluid entry opening and the fluid exit opening. The ozonated fluid passes into and out of an annulus between the core and the container. The reaction vessel processes the ozonated fluid to reduce the bubble size of the ozone gas in the ozonated fluid and to reduce the number of ozone gas bubbles in the ozonated fluid to increase the concentration of ozone in the ozonated fluid.

In other aspects, the ozonated liquid dispensing units may be integrated or incorporated into a variety of systems or platforms that spray or apply an ozonated fluid. One mobile system for producing an ozonated fluid includes an oxygen concentrator and an ozonated liquid dispensing unit connected to the oxygen concentrator to receive oxygen gas. The ozonated liquid dispensing unit includes a port for connecting to a supply of water in order to provide water for ozonation. A reaction vessel is fluidly connected to the ozonated liquid dispensing unit to process the ozonated fluid.

Another mobile system for producing an ozonated fluid includes an oxygen concentrator and a reservoir of water. The ozonated liquid dispensing unit is connected to the oxygen concentrator to receive oxygen gas, and the ozonated liquid dispensing unit is connected to the reservoir of water. A reaction vessel is fluidly connected to the ozonated liquid dispensing unit to receive ozonated fluid from the ozonated liquid dispensing unit. The reaction vessel processes the ozonated fluid. An applicator is in fluidic communication with the reaction vessel to apply the ozonated fluid.

DESCRIPTION OF FIGURES

FIG. 7 is a view showing a sprayer attached to the ozonated liquid dispensing unit.

FIG. 8 is a view of the first and second dielectric cells.

FIG. 9 is a side view of the reaction vessel.

FIG. 10 is an exploded view of the reaction vessel.

FIG. 11 is an end view of the reaction vessel.

FIG. 15 is a front view of the first mobile system.

FIG. 16 is a side view of the first mobile system.

DETAILED DESCRIPTION OF INVENTION

Figure 1:
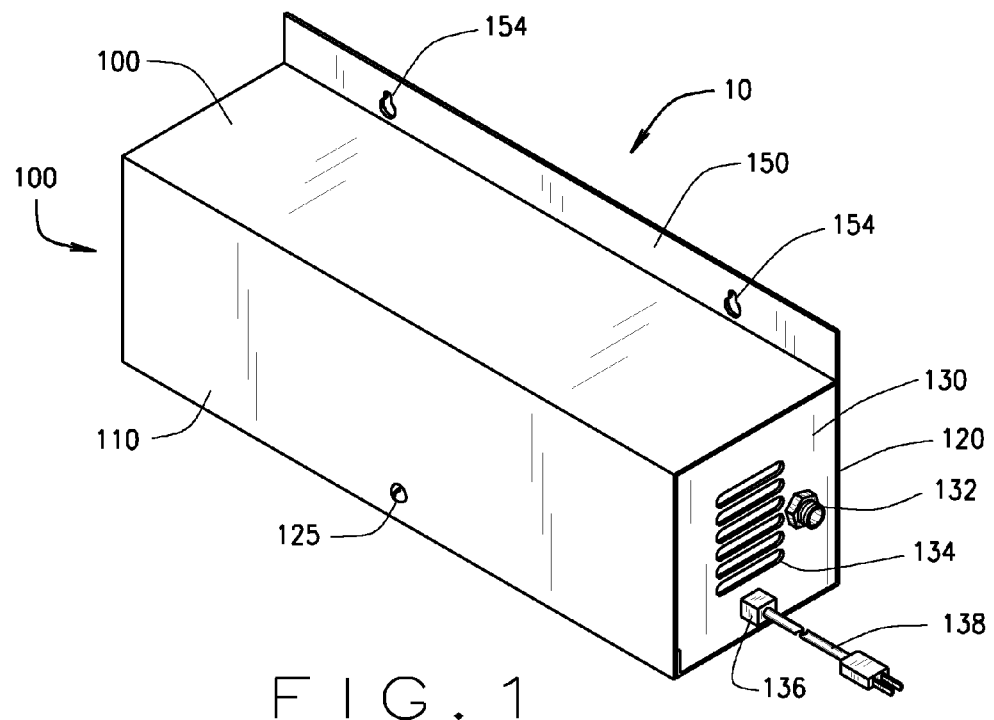
FIG. 1 shows a perspective view of the ozonated liquid dispensing unit with the output side of the unit visible.
Figure 2:
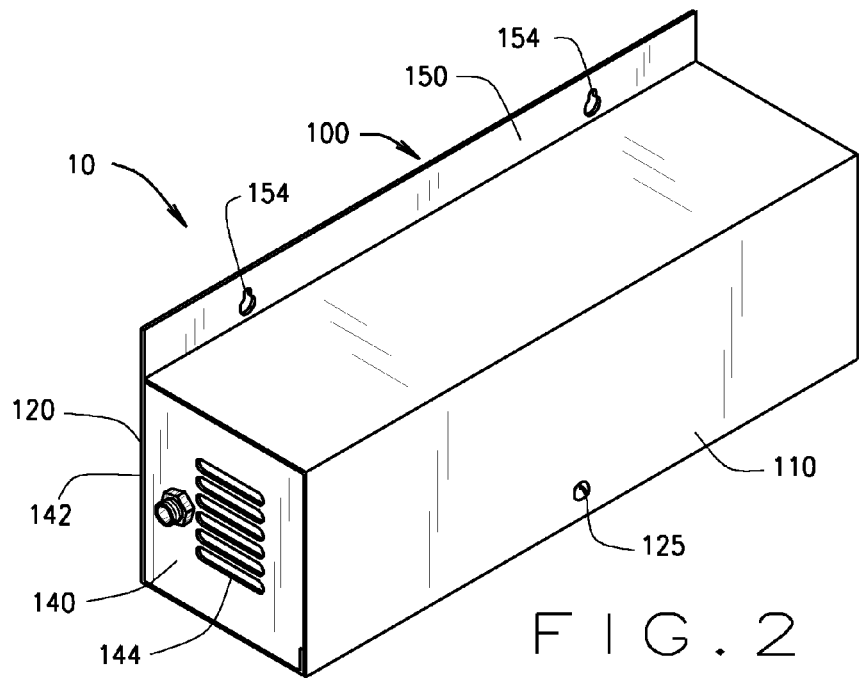
FIG. 2 is a perspective view of the ozonated liquid dispensing unit with the input side of the unit visible.

An ozonated liquid dispensing unit is described herein. With reference to FIGS. 1 and 2, an ozonated liquid dispensing unit 10 is shown. The unit 10 includes a housing 100, a removable housing cover 110 and a housing support 120. The housing 100, the housing cover 110, and the housing support 120 form a rectangular, box-like structure that houses the internal components of the unit 10. The housing 100 may be designed or engineered in other shapes and configurations. The housing 100, the housing cover 110, and the housing support 120 are made from sturdy or rugged materials, such as stainless steel, aluminum, or metals. Plastics and other composite materials may also be utilized in the construction of the housing 100, the housing cover 110 and the housing support 120.

Figure 4:
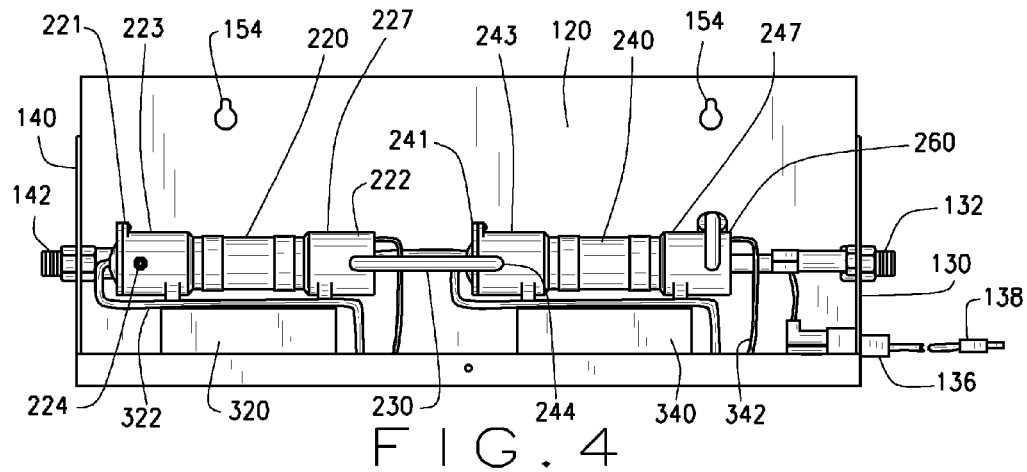
FIG. 4 is a front view of the ozonated liquid dispensing unit with the housing cover removed.
Figure 5:
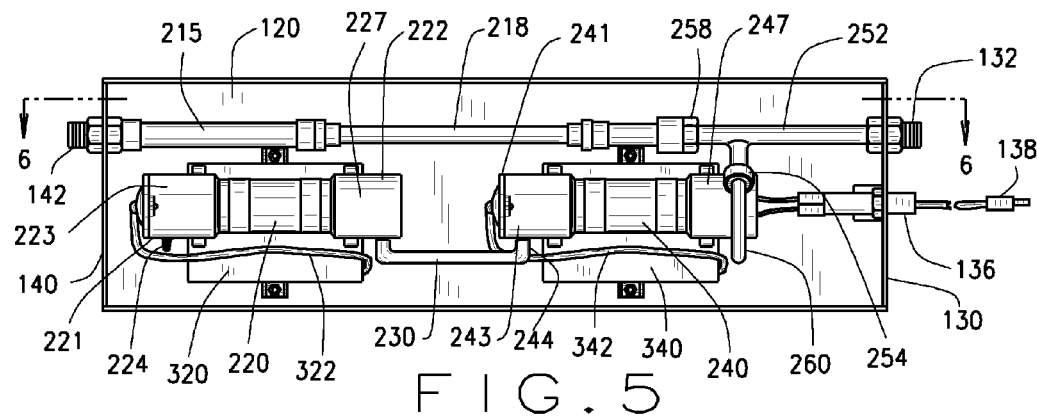
FIG. 5 is a top-down view of the ozonated liquid dispensing unit with the housing cover removed.
Figure 6:
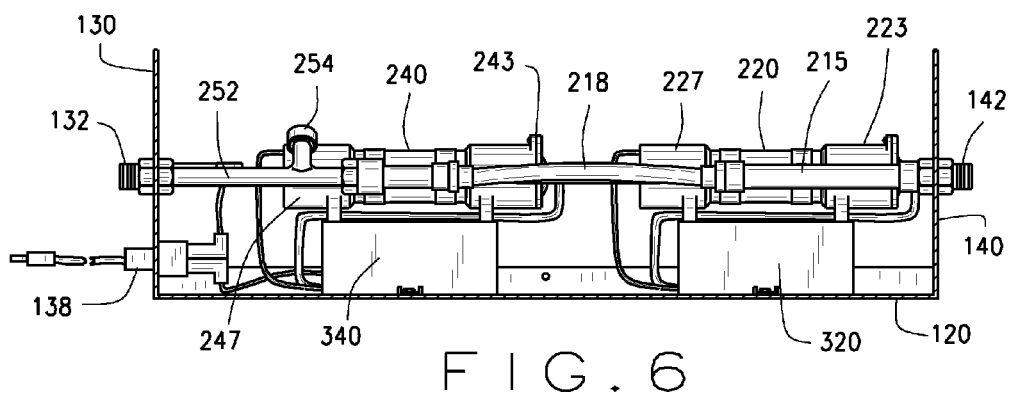
FIG. 6 is a rear view of the ozonated liquid dispensing unit with the housing cover removed.
Figure 12:
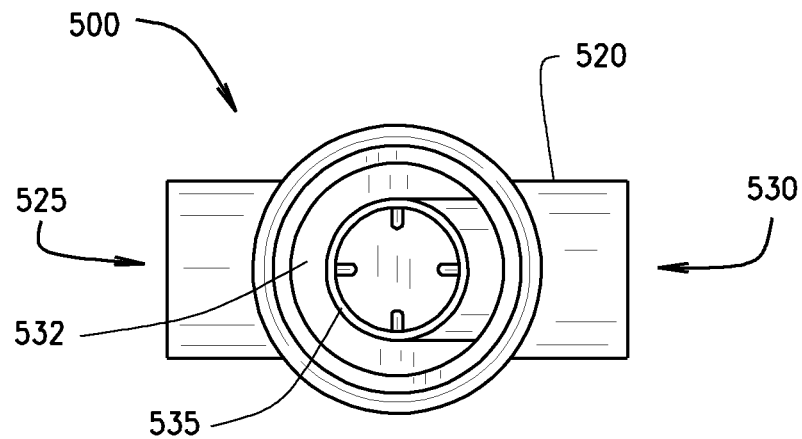
FIG. 12 is a bottom view of the reaction vessel.

As shown in FIGS. 4-6, the housing cover 110 is removed from the housing 100 to show the housing support 120, which receives and stabilizes the internal components of the unit 10. The housing cover 110 may be secured to the housing support 120 via securing means 125, such as a screw, pin, latch, lock, or other connection means for suitably attaching the housing cover 110 to the housing support 120 in a removable fashion.

FIG. 1 shows an output side 130 of the unit 10. The output side 130 includes a liquid output port 132 and an output side vent 134, and an electrical supply connection 136. The liquid output port 132 dispenses the ozonated liquid prepared in the unit 10 from the unit 10. The output side vent 134 assists in dissipating heat produced in the housing 100 from the electrical generation of ozone gas. The electrical supply connection 136 is in electrical communication with an electrical supply 138 to provide power to the unit 10.

FIG. 2 shows an input side 140 of the unit 10. The input side 140 is generally opposite of the output side 130. The input side 140 includes a liquid input port 142 and an input side vent 144. The liquid input port 142 includes threadable connections to receive a liquid input line 200 that supplies the unit 10 with water that is to be mixed with the ozone gas. The liquid input line 200 is threadably received by the liquid input port 142.

Ozonated liquid prepared by the unit 10 is discharged by the unit 10 from the liquid output port 132. A liquid output line 210 is connected to the liquid output port 132. The liquid output port 132 may include threadable connections for connecting the liquid output line 210 to the liquid output port 132. The liquid output line 210 supplies, for example, an ozone faucet 233 or other sprayer means, with a supply of the ozonated liquid.

Figure 3:
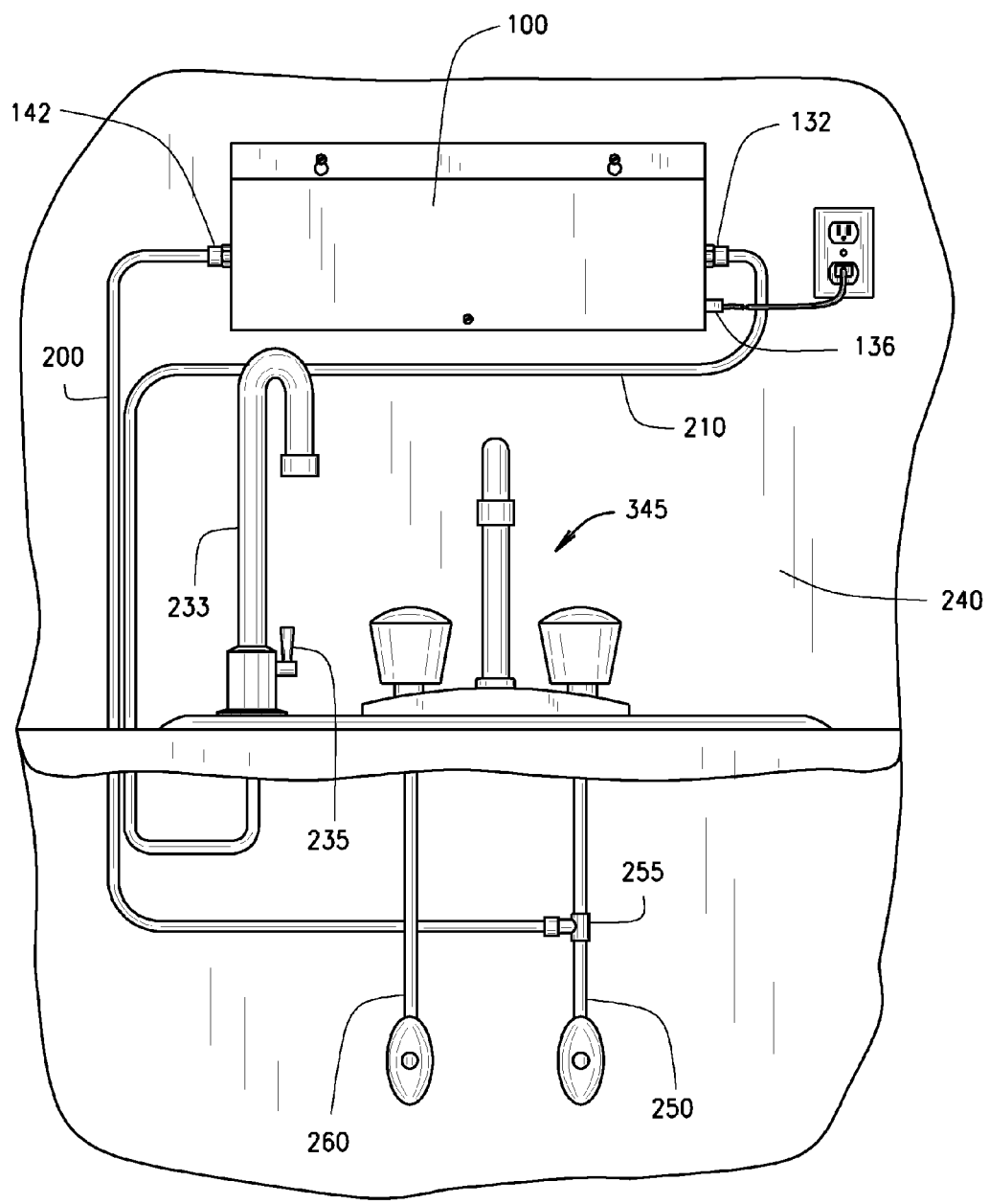
FIG. 3 is a plan diagram showing the installation of the ozonated liquid dispensing unit in conjunction with a sink and faucet.

The unit 10 may be conveniently mounted adjacent to or over a faucet/sink combination 345, such as shown in FIG. 3. The ozonated liquid may be disposed through the drain into existing waste water systems and the municipal sewer systems.

In the embodiments shown, the housing support 120 forms a flange 150 that extends beyond the housing cover 110. The flange 150 includes openings 154 which may be used to affix the unit 10 to a wall, cabinet or other structure via bolts, screws, rivets or other fastening means.

In other embodiments, the unit 10 may be placed onto a counter or underneath a counter in, for example, a kitchen cabinet or other storage area. FIG. 3 shows a diagram of unit 10 installed at the faucet/sink combination 345. During a typical installation of the unit 10, a t-shaped adaptor 255 is placed in the cold water supply 250. The adaptor 255 branches the cold water from the cold water supply 250 to the unit 10, while still providing normal cold water to the faucet/sink combination 345. The adapter 255 supplies fresh, cool water via the liquid input line 200 to the unit 10. The adapter 255 does not interrupt flow of the cool water supply 250 to the faucet/sink combination 345. A hot water supply 260 typically does not receive, or is involved with, the preparation of the ozonated liquid by the unit 10.

As ozone gas is created by the unit 10 and the ozone gas is mixed into the cold water entering the unit 10 from the cold water supply 250, the ozonated liquid is discharged at the liquid output port 132. The liquid output port 132 is in fluidic communication with an ozone faucet 233 via the liquid output line 210. By turning on a handle 235 of the ozone faucet 233, water is drawn into and through the unit 10 where ozonated gas prepared in the unit 10 is mixed with the water. During operation of the unit 10, the operator only needs to pull on the handle 235 in order for ozonated liquid to be discharged from the ozone faucet 233. The unit 10 does not require other manual actuation each time the unit 10 is used, i.e., the operator need not actuate an on/off switch or the like.

The internal components of the unit 10 are shown in FIGS. 4-6. Water from the cool water supply 250 enters a fluid flow switch 215, which activates the unit 10 upon sensing a flow of water. The fluid flow switch is in fluidic communication with an injector 252 via a liquid line 218.

The liquid line 218 fluidly connects the fluid flow switch 215 with the injector 252. The liquid line 218 may comprise a hose, plastic tubing, metal braided tubing, or other suitable structure for communicating liquid from the fluid flow switch 215 to the injector 252.

The water supplied to the injector 252 is mixed with ozone gas from the first dielectric cell 220 and the second dielectric cell 240. As further described herein, the first dielectric cell 220 supplies supply gas containing ozone gas to the second dielectric cell 240. The second dielectric cell 240 creates additional ozone gas in the supply gas and supplies the ozone gas to the injector 252, and the injector 252 mixes the ozone gas into the water in order to form the ozonated liquid that is discharged from the unit 10 at the liquid output port 132.

The injector 252 forms the ozonated liquid by mixing ozonated gas with the water. Suitable injectors are commercially available from the Mazzei Injector Corporation. The injector 252 uses a pressure differential between the water entering the injector 252 from the liquid line 218 and the fluid exiting the injector 252 to mix the water with ozone gas. The pressure at an inlet port of the injector 252 is higher than the pressure at an outlet port of the injector 252, and this pressure differential creates a suction in the injector 252 that draws the ozone gas from the second dielectric cell 240 into the injector 252 for mixing with the water.

An important feature of the unit 10 is the use of multiple dielectric cells, namely, the first dielectric cell 220 and the second dielectric cell 240. The first dielectric cell 220 prepares ozone gas that is supplied to the second dielectric cell 240, which creates additional ozone gas, thus creating a highly concentrated supply of ozone gas that is supplied to the injector 250. In other embodiments, additional dielectric cells may be employed.

With reference to FIG. 5, top-down view of the unit 10 is shown. Ambient air is drawn into the first dielectric cell 220 via an ambient air input 224 of a first gas input trap 223. The first gas input trap 223 is sealingly connected to and surrounds a first end 221 of the first dielectric cell 220. The first dielectric cell 220 makes ozone gas from the ambient air passing through the first dielectric cell 220.

The first dielectric cell 220 includes a glass or other insulating cylinder. An electrical conductor passes through the cylinder. A conductive metal lattice, metal mesh, or coil wire surrounds the conductor. When power is supplied to the first dielectric cell 220, electricity passes through the conductor and sparks and arcs. This electrical discharge splits the oxygen molecules creating ozone gas from the oxygen molecules present in the ambient air inside of the dielectric cell 220. This method is generally referred to as corona discharge. The second dielectric cell 240 is constructed similar to the first dielectric cell 220.

As described above, ozone gas created by the coronal discharge in the first dielectric cell 220 is captured and supplied to the second dielectric cell 240. The supply gas from the first dielectric cell 220 to the second dielectric cell 240 contains an amount of ozone gas. A second or output end 222 of the first dielectric cell 220 is sealingly connected to and surrounded by a first gas output trap 227. The first gas output trap 227 funnels the ozone gas created by the first dielectric cell 220 to a first gas line 230 which is in fluidic communication with a second gas input trap 243 and an ozone gas input 244 on the second gas input trap 243. The first gas line 230 thus connects to the first gas output trap 227 to the ozone gas input 244. The second gas input trap 243 is sealingly connected to a first or input end 241 of the second dielectric cell 240. As such, supply gas to the second dielectric cell 240 already includes a first amount of ozone gas. The supply gas from the first dielectric cell 220 is further processed by the second dielectric cell 240 to add an additional amount of ozone gas to the supply gas.

The first gas output trap 227 seals the output of ozone gas from the first dielectric cell 220 such that nearly all of the ozone gas created by the first dielectric cell 220 or the output of gas from the first dielectric cell 220 is supplied in a closed communication via the first gas line 320 to the second dielectric cell 240. The closed communication provides for the second dielectric cell 240 to form ozone gas from the output gas of the first dielectric cell 220.

The ozonated gas produced by the second dielectric cell 240 is transported via a second gas line 260 to an injector gas input port 254 of the injector 252. The second gas output trap 247 is sealingly connected to a second or output end 242 of the second dielectric cell 240.

The use of the first and second dielectric cell 220 and 240 creates an increased concentration of ozone gas in supply communication with the injector 252. A single dielectric cell similar to the first dielectric cell 220 or the second dielectric cell 240 creates ozone gas at a concentration of 0.5 parts per million. However, the use of two of the two inline dielectric cells, i.e., the first dielectric cell 220 and the second dielectric cell 240, creates a supply of ozone gas to the injector 252 having a concentration of approximately 1.3 ppm of ozone.

The unit 10 is electrically connected to the power supply 138, such as a 115-volt power supply. The electrical connector 136 of the unit 10 is in electrical communication with a first power supply 320 and a second power supply 340. A first electrical supply line 322 is in electrical communication with the first power supply 320 and at a conductor positioned at the first end 221 of the first dielectric cell 220. A second electrical supply line 342 is in electrical communication with the second power supply 340 and at a conductor positioned at the first end 241 of the second dielectric cell 240. The electrical supply lines 322 and 342 provide the electricity for the corona discharge.

Turning now to FIG. 7, the ozone faucet 233 has been replaced with a spray nozzle 400 having a handle 410 to actuate the discharge of the ozonated liquid. The spray nozzle 400 is in fluidic communication with the liquid output port 132. A hose, tube or other liquid communication structure 405 is used to supply the sprayer 400 with the ozonated liquid from the liquid output port 132. The spray nozzle 400 or the liquid communication structure 405 includes a valve means or other shut-off to control the output of liquid from the spray nozzle. For example, a handle 410 of the spray nozzle 400 may actuate the valve or otherwise control the flow of the ozonated liquid from the spray nozzle 400. The spray nozzle 400 may be used to spray fruits and vegetables in order to kill microorganisms, remove dirt and debris, and/or wash of pesticide residue.

The spray nozzle 400 may further be used to clean and sanitize shower areas and rest rooms. Spraying the ozonated liquid onto such bathroom surfaces is an economical and convenient method to provide for sanitation. The ozonated liquid does not leave a residue or film on the restroom and shower surfaces. No other chemicals or detergents are required. There is no clean-up or storage of soiled conventional cleaning tools, such as a mop or mop bucket.

The unit 10 provides a flow of ozonated liquid at approximately 25 psi and 1.5 gallons per minute from the ozone faucet 233 or the spray nozzle 400. The ozonated liquid has an ozone concentration of approximately 1.8 parts per million.

The unit 10 also finds utility in cleaning fruits and vegetables. Herbicide residue may be removed from the fruit and vegetable surfaces. Pathogens, such as *salmonella*, may be easily removed from more delicate food surfaces, such as that of a tomato. Raw meats and carcasses and may also be directly contacted with the ozonated liquid.

The unit 10 may also be used to clean and sterilize medical instruments. The unit 10 may also be used for general hand-washing and wound-flushing. The unit 10 may also be used for drain cleaning. The oxidation provided by the ozonated liquids will break-up many deposits in drains.

In operation of the unit 10, the user actuates the handle 235 of the ozone faucet 233. When the cold water begins to flow through the liquid input line 200 to the unit 10, the liquid flow switch 215 activates the first power supply 320 and the second power supply 340 to discharge electrical current to the first dielectric cell 220 and the second dielectric cell 240 to the begin creation of ozone gas. Generally, the operator should expect to wait several seconds for the water flowing from the ozone faucet 233 to transition to ozonated liquid. When the handle 235 is turned off, water flow through the unit 10 is stopped and the liquid flow switch 215 turns the first power supply 320 and the second power supply 340 off.

A reaction vessel 500 is shown in FIGS. 9-13. The reaction vessel 500 may be used to process ozonated fluid to reduce the bubble size of the ozone gas in the ozonated fluid. The reaction vessel 500 may be connected to the output of an ozonated liquid dispensing unit. The reaction vessel 500 receives the ozonated fluid, processes the ozonated fluid, and outputs the processed ozonated fluid. Faucets, sprayers, applicators, and other dispensing systems may receive the ozonated fluid from the reaction vessel 500. For example, the reaction vessel 500 may be used with the ozonated liquid dispensing unit 10 shown in FIGS. 1-8. For example, the reaction vessel 500 may be used with the ozonated liquid dispensing unit 10 shown in FIG. 3 and plumbed into the faucet/sink combination 345.

Figure 14:
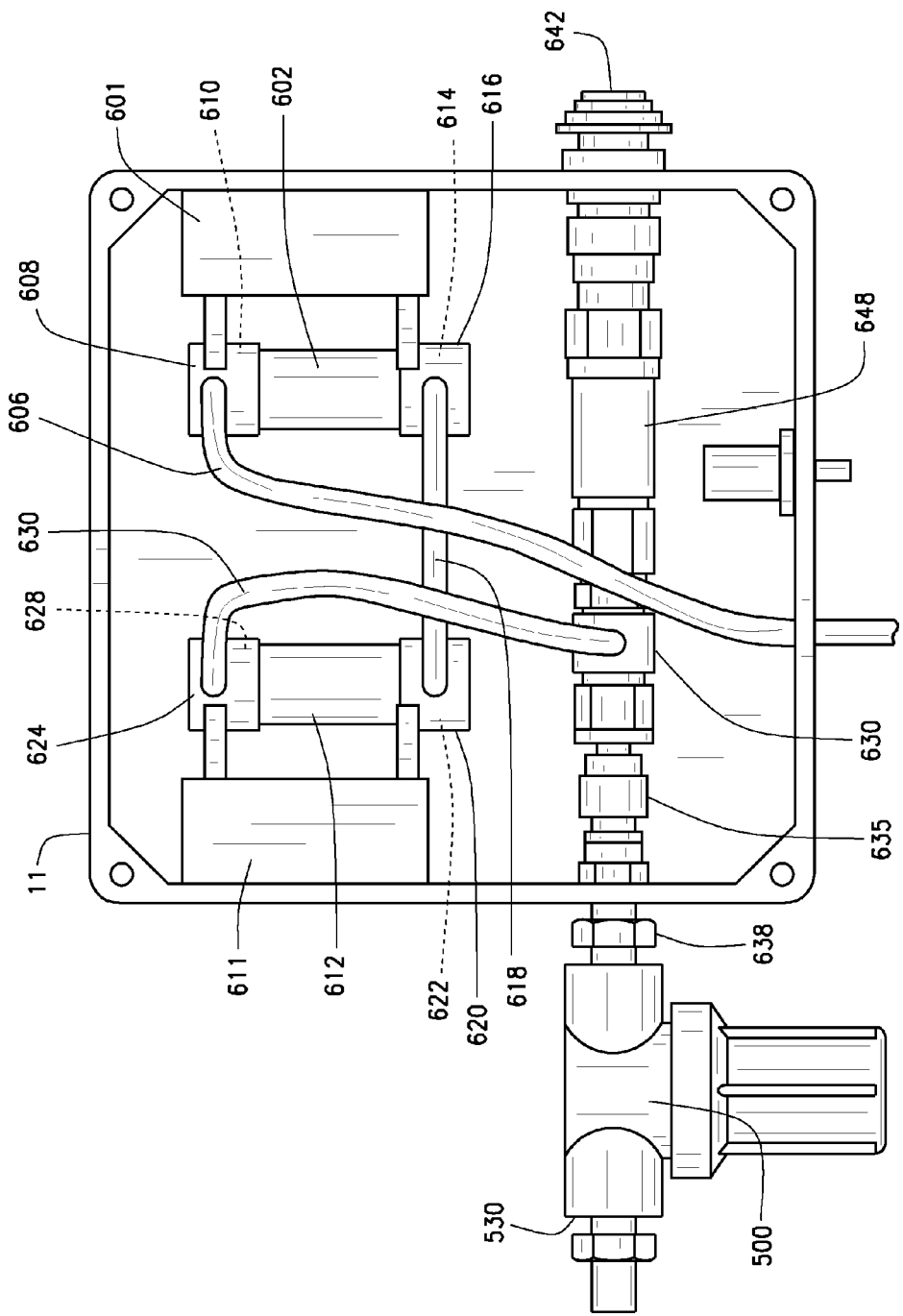
FIG. 14 is a top-down view of the ozonated liquid dispensing unit with the reaction vessel attached.
Figure 17:
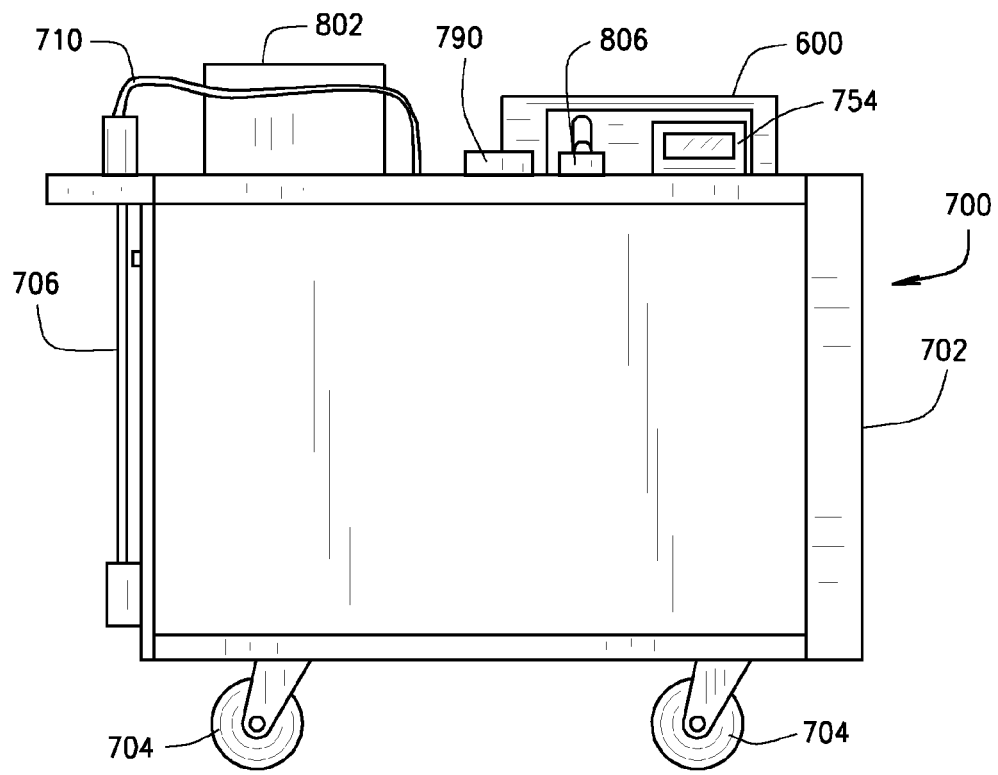
FIG. 17 is a front view of the second mobile system.
Figure 18:
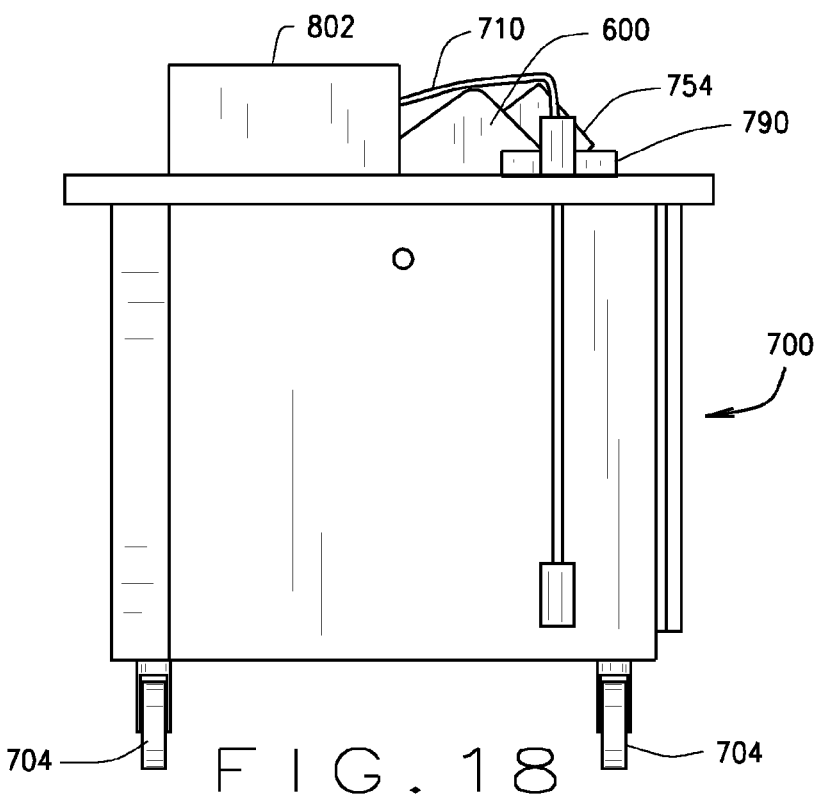
FIG. 18 is an end view of the second mobile system.

A further embodiment of the ozonated liquid dispensing unit is shown in FIG. 14. An ozonated liquid dispensing unit 11 is shown with the reaction vessel 500 in FIG. 14. The ozonated liquid dispensing unit 11 generally operates in a similar manner to the ozonated liquid dispensing unit 10, which is shown in FIGS. 1-8. The ozonated liquid dispensing unit 11 is described below in greater detail.

As shown in FIG. 14, the reaction vessel 500 is in fluidic communication with a liquid output port 638 of the ozonated liquid dispensing unit 11. The liquid output port 638 discharges the ozonated fluid prepared by the ozonated liquid dispensing unit 11 into the reaction vessel 500 for processing.

The reaction vessel 500 further processes the ozonated fluid to reduce the bubble size of the ozone gas in the ozonated fluid. The reaction vessel 500 further reduces the number of ozone gas bubbles in the ozonated fluid to increase the concentration of ozone in the ozonated fluid. Decreasing the bubble size of the ozone gas also assists in maintaining a uniform concentration of ozone gas in the ozonated fluid. The processing by the reaction vessel 500 and its components are further described below.

Figure 13:
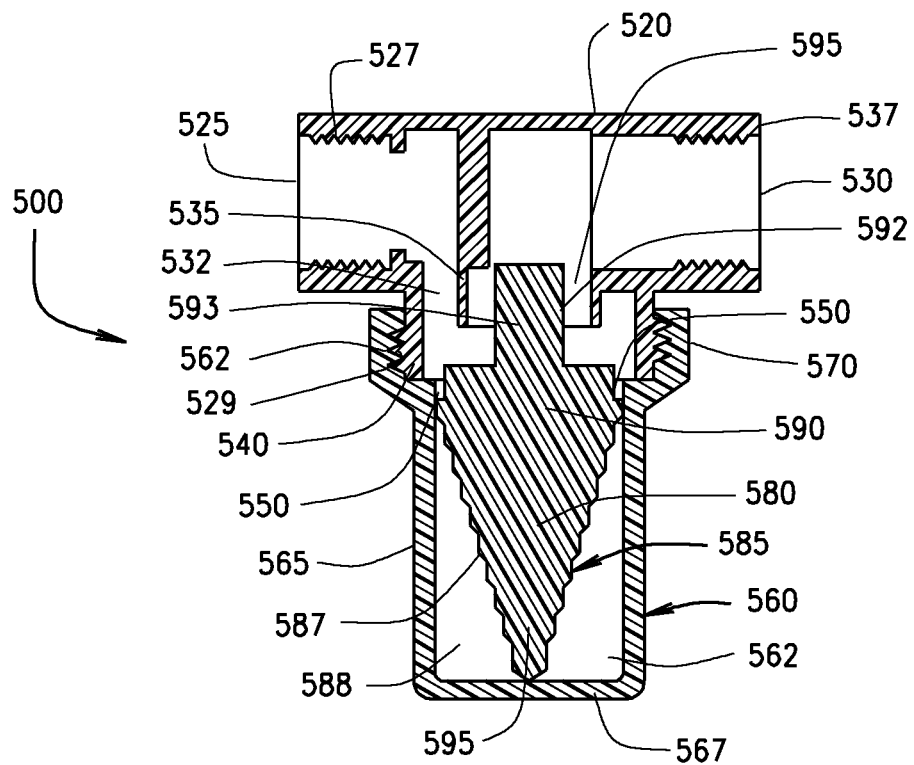
FIG. 13 is a cross-sectional view of the reaction vessel.

As shown in FIG. 13, the reaction vessel 500 includes an assembly 520 that receives a container 560, which defines an open volume 562. The container 560 forms a cup-like structure to hold the core 580. The container 560 has container walls 565 that help to position the core 580. The container 560 contains the core 580 in the open volume 562. The container 560 defines a container rim 570 that engages the assembly 520.

Generally, the ozonated fluid from the liquid output port 132 of the unit 10 or the liquid output port 638 of the unit 11 enters a fluid entry opening 525 of the assembly 520 and the ozonated fluid passes into the container 560, where it is processed about the core 580. Then, the processed ozonated fluid exits the assembly 520 via the fluid exit opening 530 and to the sprayer 400, other sprayers, other systems, or other distributors and/or applicators.

The assembly 520 receives the container 560 in a threadable engagement. As shown in FIG. 10, a lower assembly wall 540 of the assembly 520 includes assembly threads 529. The assembly threads 529 are in a threadable engagement with container threads 562 of the container rim 570. The container 560 is threadably attached or connected to the assembly 520 via the engagement of the container threads 562 and the assembly threads 529.

The container 560 includes container walls 565 that surround the core 580. An annulus 588 in the open volume 562 is provided between the container walls 565 and the core 580. The annulus 585 provides a space for the ozonated fluid to circulate about the core 580.

The core 580 includes a solid, cone-shaped structure. The ozonated fluid circulates about a ridged surface 585 of the core 580. The core 580 includes a wider portion 590 closer to the container rim 570, and the core 580 includes a narrower portion 595 near a bottom 567 of the container 570. The wider portion 590 is close to or just less than in size compared to an internal diameter of the container 560. An annular gap 550 is located between the wider portion 590 and the container wall 565. The fluid entry opening 525 is in fluidic communication with the annulus 588 via the annular gap 550. The fluid exit opening 530 is in fluidic communication with the annulus 588 via the annular gap 550.

An outer surface of the core 580 includes the ridged surface 585. The ridged surface 585 includes a plurality of ridges 587 that assist in crushing and breaking the bubbles of ozone gas in the ozonated fluid as the ozonated fluid circulates and swirls about the ridged surface 585. In the embodiment shown in FIG. 10, the ridged surface 585 includes approximately 9 to approximately 12 ridges 587. Other embodiments may include approximately 5 to approximately 30 ridges 587. The number of ridges 587 provided on the ridged surface 585 will vary depending upon the size of the core 580 and the reaction vessel 500, the amount of fluid to be processed in the reaction vessel 500, as well as other variables. The core 580 further includes a stem 593 extending from the wider portion 590. The core 580 extends into a fluid exit outlet 535 of the assembly 520.

The ozonated fluid from the ozonated liquid dispensing unit 11 enters the reaction vessel 500 at the fluid entry opening 525. The fluid entry opening 525 may include threads 527 to threadably engage to a liquid output port 638 of the ozonated liquid dispensing unit 11. In other embodiments, a hose or fluid line may connect the ozonated liquid dispensing unit 11 and the reaction vessel 500.

The ozonated fluid passes through a fluid entry passage 532 of the reaction vessel 500 that is defined by the lower assembly wall 540 and the fluid exit outlet 535. The lower assembly wall 540 extends downward between the fluid entry opening 525 and the fluid exit opening 530. The ozonated fluid next passes through the annular gap 550 between the ridged surface 585 of the wider portion 590 of the core 580 and the container wall 565. The ozonated fluid next circulates and flows about the interior of the container 560 in the annulus 588.

The ozonated fluid is under pressure from the flow of fluid through the ozonated liquid dispensing unit 11. This pressure urges the ozonated fluid to contact the ridged surface 585, which crushes and reduces the size of ozone gas bubbles in the ozonated fluid. The ozonated fluid next exits the container 560 through the annular gap 550 and enters an annular fluid exit passage 595 of the fluid exit outlet 535. The fluid exit outlet 535 is in fluidic communication with the fluid exit opening 530. The ozonated fluid then passes through the fluid exit opening 530 and onto the fluid supply line 405, sprayer, hoses, lines, or distribution assembly. The fluid exit opening 530 may include threads 537 to engage to such spraying and/or distribution structures.

The fluid exit outlet 535 defines the annular fluid exit passage 595, which is the opening between the walls forming the fluid exit outlet 535 and an outer circumference 592 of the stem 593 of the core 580. The stem 593 is loosely positioned in the fluid exit outlet 535. The loose engagement of the stem 593 into the fluid exit outlet 535 assist in maintaining an upright position for the core 580.

The assembly 520, the core 580 and the container 560 may be constructed from a variety of materials, such as plastics, metals or metal alloys. The assembly 520, the container 560 and the core 580 are well suited for manufacturing by injection molding. The container 560 may further clamp or snap fit onto the assembly 520.

The ozonated liquid dispensing units 10 and 11 may be incorporated into a variety of systems, applicators, platforms, etc. that are suitable for use in a variety of applications, industries, and manners that use, spray, apply or otherwise utilize an ozonated fluid in order to clean, sanitize, disinfect, etc. For example, the ozonated liquid dispensing units 10 and 11 may be incorporated into portable kitchen systems, mobile hospital cleaning equipment, floor/carpet cleaners, air scrubbers, etc.

The ozonated liquid dispensing unit 11 will now be described with reference to FIG. 14. The ozonated liquid dispensing unit 11 functions similarly to the ozonated liquid dispensing unit 10, i.e., feed gas is passed through two ozone generators arranged in a serial manner with the output gas from a first ozone generator supplying the second ozone generator. The ozonated liquid dispensing unit 11 may be used with or without the reaction vessel 500 shown in FIGS. 9-13. Of course, the use of the reaction vessel 500 will provide an ozonated solution with improved cleaning and sanitizing characteristics.

Oxygen gas is produced by an oxygen concentrator or generator 600. The oxygen gas is drawn into a first dielectric cell 602 via a first gas line 606. A first oxygen gas input trap 608 is sealingly connected to and surrounds a first end 610 of the first dielectric cell 602. The first gas line 606 connects the oxygen has input trap 608 and the oxygen concentrator 600. The first dielectric cell 602 makes ozone gas from the oxygen gas passing through the first dielectric cell 602.

Similar to the other embodiments described herein, the first dielectric cell 602 includes a glass or other insulating cylinder. An electrical conductor passes through the cylinder. A conductive metal lattice, metal mesh, or coil wire surrounds the conductor. When power is supplied to the first dielectric cell 602, electricity passes through the conductor and sparks and arcs. This electrical discharge splits the oxygen molecules creating ozone gas from the oxygen molecules present in the ambient air inside of the first dielectric cell 602. This method is generally referred to as corona discharge. A second dielectric cell 612 is constructed similar to the first dielectric cell 602. Power cells 601 and 611 supply the first and second dielectric cells 602 and 612 with the power.

As described above, ozone gas created by the coronal discharge in the first dielectric cell 602 is captured and supplied to the second dielectric cell 612. The supply gas from the first dielectric cell 602 to the second dielectric cell 612 contains an amount of ozone gas. A second or output end 614 of the first dielectric cell 602 is sealingly connected to and surrounded by a first gas output trap 616. The first gas output trap 616 funnels the ozone gas created by the first dielectric cell 602 to a second gas line 618 which is in fluidic communication with a second gas input trap 620. The second gas line 618 thus connects to the first gas output trap 616 and to the second gas input trap 620. The second gas input trap 620 is sealingly connected to a first or input end 622 of the second dielectric cell 240. As such, supply gas to the second dielectric cell 612 already includes a first amount of ozone gas. The supply gas from the first dielectric cell 602 is further processed by the second dielectric cell 612 to add an additional amount of ozone gas to the supply gas.

The first gas output trap 616 seals the output of ozone gas from the first dielectric cell 602 such that nearly all of the ozone gas created by the first dielectric cell 602 or the output of gas from the first dielectric cell 602 is supplied in a closed communication via the second gas line 618 to the second dielectric cell 612. The closed communication provides for the second dielectric cell 612 to form ozone gas from the output gas of the first dielectric cell 602.

The second gas output trap 624 is sealingly connected to a second or output end 628 of the second dielectric cell 612. The ozonated gas produced by the second dielectric cell 612 is transported via a third gas line 630 to the injector 630.

The ozonated liquid dispensing unit 11 further includes the injector 630. The injector 630 may be a chemical injector commercially available from Dultmeier Sales in Omaha, Nebraska, under the trade name, Chem Flex Injectors as part number HF 110057. The injector 630 uses a check-ball to prevent backflow into the injector 630.

Water enters a liquid input port 642. The water is directed through a fluid flow switch 648, which activates the first dielectric cell 602 and the second dielectric cell 612. A suitable flow switch for the fluid flow switch 648 include a Series 5 Erecta Switch from OKI Sensor Device Corporation. Next, the water passes to the injector 630, which injects the water with the ozone gas. The injector 630 accommodates flow rates through the ozonated liquid dispensing unit 11. The supply of fresh water to the ozonated liquid dispensing unit 11 may vary depending on other uses in the water supply system, seasonal changes in water pressure, as well as other peak and off peak usage levels of the fresh water. From the injector 630, the ozonated fluid passes to fluidic connectors 635 which pass the ozonated fluid to the reaction vessel 500 via a liquid output port 638.

The ozonated liquid dispensing unit 11 provides a flow rate of approximately ½ gallon per minute to approximately 15 gallons per minute at a concentration of approximately 0.05 ppm to approximately 5 ppm. The ozonated liquid dispensing unit 11 may be scaled up or down to increase or decrease the amount of flow of ozonated fluid. The ozonated liquid dispensing unit 11 may be integrated or incorporated into a variety of systems or platforms that spray or apply an ozonated fluid.

As described above, the ozonated liquid dispensing units 10 and 11 may be incorporated into a variety of systems, applicators, platforms, etc. that use an ozonated fluid in order to clean, sanitize, disinfect, etc.

A first mobile system 650 is shown in FIGS. 15-16. The first mobile system 650 fluidly connects to a supply of water, such as a spigot, faucet, or other water source. The first mobile system 650 also electrically connects to a source of power in order to operate the first mobile system 650. A second mobile system 700 is shown in FIGS. 17-20. The second mobile system 700 includes a tank of water to supply the ozonated liquid dispensing units 10 or 11 for making the ozonated liquid. The second mobile system 700 includes batteries to power the system, which provides for the second mobile system 700 to be moved from room to room or from area to area in a hospital, hotel, or other large building.

The first mobile system 650 will now be described in detail with reference to FIGS. 15-16. The first mobile system 650 may be used as a remote and portable producer of ozonated fluid. The first mobile system 650 is well-suited to be used in a mobile kitchen for cleaning and sanitizing food, dishes, cooking utensils, as well as for general cleaning and handwashing. Ozonated fluid is suitable for direct food contact. The first mobile system 650 may be used anywhere there is a supply of water and electricity.

A housing 652 of the first mobile system 650 is shown in FIGS. 15 and 16. The housing 652 includes the ozonated liquid dispensing unit 11 integrated or connected with the oxygen concentrator 600. The oxygen concentrator 600 outputs oxygen gas at an outlet 655. A hose 660 directs the oxygen gas from the outlet 655 to the ozonated liquid dispensing unit 11. Tubing or other fluidic connections may be used to connect the outlet 655 to the ozonated liquid dispensing unit 11 in order to supply oxygen gas. Water is also directed to the ozonated liquid dispensing unit 11 via the liquid input port 642. The ozonated fluid is dispensed from the first mobile system 650 at the fluid exit opening 530.

The first mobile system 650 includes the housing 652. In the embodiment shown, the ozonated liquid dispensing units 11 is mounted externally on the housing 652. In other embodiments, the ozonated liquid dispensing units 11 is incorporated internally or partially in the housing 652.

The first mobile system 650 includes the oxygen concentrator 600. The oxygen concentrator 600 prepares a supply of feed oxygen gas from ambient air. The feed oxygen gas is supplied to the ozonated liquid dispensing units 10 or 11. The feed oxygen gas has a higher concentration of oxygen as compared to the ambient air. The oxygen concentrator 600 lessens the effects of temperature and humidity on the preparation of the ozonated gas in the ozonated liquid dispensing units 10 or 11.

An on/off switch 672 turns the oxygen concentrator 600 on and off. A flow gauge 674 indicates oxygen gas flow rate. A control knob 676 adjusts the flow rate of the oxygen gas. A circuit breaker reset button 678 resets the oxygen concentrator 600.

A suitable oxygen concentrator 600 is commercially available from the AIRSEP Corporation as the NEW LIFE model, which provides an approximate 2 liter per minute flow of 98% oxygen. Oxygen concentrators are described in U.S. Pat. Nos. 6,908,503 and 5,871,564, which are hereby incorporated by reference in their entirety. Such oxygen concentrators operate by pressure swing adsorption techniques to concentrate oxygen out of the ambient air. The oxygen concentrators use one or more adsorbers, each having a fixed sieve bed of adsorbent material to fractionate at least one constituent gas from a gaseous mixture by adsorption into the bed, when the gaseous mixture from a feed stream is sequentially directed through the adsorbers in a co-current direction. While one adsorber performs adsorption, another adsorber is simultaneously purged of its adsorbed constituent gas by part of the product gas that is withdrawn from the first or producing adsorber and directed through the other adsorber in a counter-current direction. Once the other adsorber is purged, the feed stream at a preset time is then directed to the other adsorber in the co-current direction, so that the other adsorber performs adsorption. Ambient air is supplied to the apparatus by a fan used to draw air into the interior of the oxygen concentrator. The air is moved by a feed air compressor/heat exchanger assembly alternatively to first and second adsorbers through feed valves respectively.

The first mobile system 650 includes an electrical plug to electrically connect to a source of electricity, such as 110 V alternating current.

The first mobile system 650 provides an ozonated liquid with a ozone concentration of approximately 5 ppm at a flow rate of approximately 2 gallon per minute.

In other embodiments, mobile systems are provided that produce an ozonated fluid and are conveniently moved to different locations without the need for access to dedicated electrical power in each of the different locations. Such mobile systems include an oxygen concentrator supplying ozonated liquid dispensing units, such as the ozonated liquid dispensing units 10 and 11, in order to prepare ozonated fluid. The mobile systems may include batteries, such as rechargeable batteries, in order to operate the system as the system is moved from location to location. The mobile systems may be recharged at night, when not in use. The mobile systems include an applicator, such as a wand with a nozzle, in order to apply the ozonated fluid. Preferably, the applicator, such as the wand and nozzle, atomizes the ozonated fluid into a mist that may be sprayed onto walls, floors, and other surface. The mobile systems may be used spray the mist directly onto mattresses, pillows curtains, soft goods, entire bathrooms, etc. in order to clean and sanitize and sanitize such articles and surfaces.

The applicator may include a regulator to relieve back-pressure on the applicator to assist in stopping droplets or beads of ozonated fluid from forming. Also, the regulator helps relieve back-pressure to prevent the ozonated gas from separating from the ozonated fluid at the applicator.

The second mobile system 700, shown in FIGS. 17-20, will now be described in detail. The second mobile system 700 includes a tank 712 to hold approximately 5 to approximately 40 gallons of water or other fluid. The ozonated fluid is made on demand by the second mobile system 700 from the water or fluid in the tank 712.

The second mobile system 700 includes a housing 702. Wheels 704 may be attached or integral with the housing 702 to provide mobility for the second mobile system 700. Casters or other rollers may be used with or instead of the wheels 704.

A wand 706 is in fluidic communication with the second mobile system 700 via a hose 710. The wand 706 may be used to spray a mist or atomize ozonated fluid prepared by the second mobile system 700. The wand 706 includes a spray head, tip or other applicator that sprays or atomizes the ozonated fluid. In other embodiments, the hose 710 may connect directly to the spray head, tip or other applicator for spraying or atomizing the ozonated fluid.

The second mobile system 700 includes the tank 712 to act as a reservoir or storage for water and/or to receive ozonated fluid that is not sprayed by the wand 706. Water may be added to the tank 712 via a cap 716 that covers or closes an opening to the tank 712.

A fluid line 720 connects the tank 712 and a pump 728. The pump 728 draws the fluid from the tank 712 and directs the fluid to the ozonated liquid dispensing unit 11. The fluid line 720 may include an isolation valve 724 to open and close the fluid line 720. A suitable pump for the pump 728 includes a model #02100-022 FLOJET pump.

A fluid line 730 connects the pump 728 and the ozonated liquid dispensing unit 11. A pressure regulator 734 controls the pressure of the fluid provided to the ozonated liquid dispensing unit 11 via the fluid line 730.

The ozonated liquid dispensing unit 11 is in communication with the oxygen concentrator 600 to supply the ozonated liquid dispensing unit 11 with oxygen for making ozone gas. The ozone gas is injected into the fluid received via the fluid line 730. The ozonated liquid dispensing unit 11 includes the reaction vessel 500 that outputs the ozonated fluid at a fluid line 740.

The fluid line 740 is in fluidic communication with a sensor 750. The fluid line 740 further includes a check valve 744. The sensor 750 monitors the oxidation reduction potential for the ozonated fluid. The sensor 750 is in electrical communication with an oxidation reduction potential monitor 754 via an electrical line 725. From the sensor 750, the ozonated fluid passes via a fluid line 755 to a splitting connection 760.

The splitting connection 760 splits the ozonated fluid to a fluid line 775 and to the hose 710. A regulator 770 in the fluid line 775 controls how much fluid is directed to the hose 710. The regulator 770 controls and adjusts the volume of ozonated fluid that is passed to the hose 710. The regulator 770 includes an adjustment knob 780 that may be turned by the operator to increase or reduce the pressure of the ozonated fluid passing to the wand 706. The regulator 770 may be fully closed, and, as such, all of the fluid from the fluid line 755 is directed to the hose 710. The regulator 770 may also be opened or closed incrementally to send increasing or decreasing amounts of ozonated fluid to the hose 710. Ideally, the second mobile system 700 is spraying a mist, i.e., a solution that will not run on a vertical wall. If too much pressure is provided to the wand 706, then the ozonated fluid may be sprayed in too rapid of a manor and thus create droplets or large beads of ozonated fluid. As such, the operator may turn the knob 780 to regulate the spray of the ozonated fluid from the wand 706 in order to achieve the desired misting.

The fluid line 775 provides a return of the ozonated fluid from the regulator 770 back to the tank 712 for reuse. As such, the system 700 recycles the ozonated fluid that was not sprayed from the wand 706. The ozonated fluid that is returned to the tank 712 is reused by the second mobile system 700.

The tank 712 includes a low level sensor 785 that is in electrical communication with and alarm 790 via an electrical line 787. When the fluid level in the tank 712 falls to low, then alarm 790 is activated.

Figure 19:
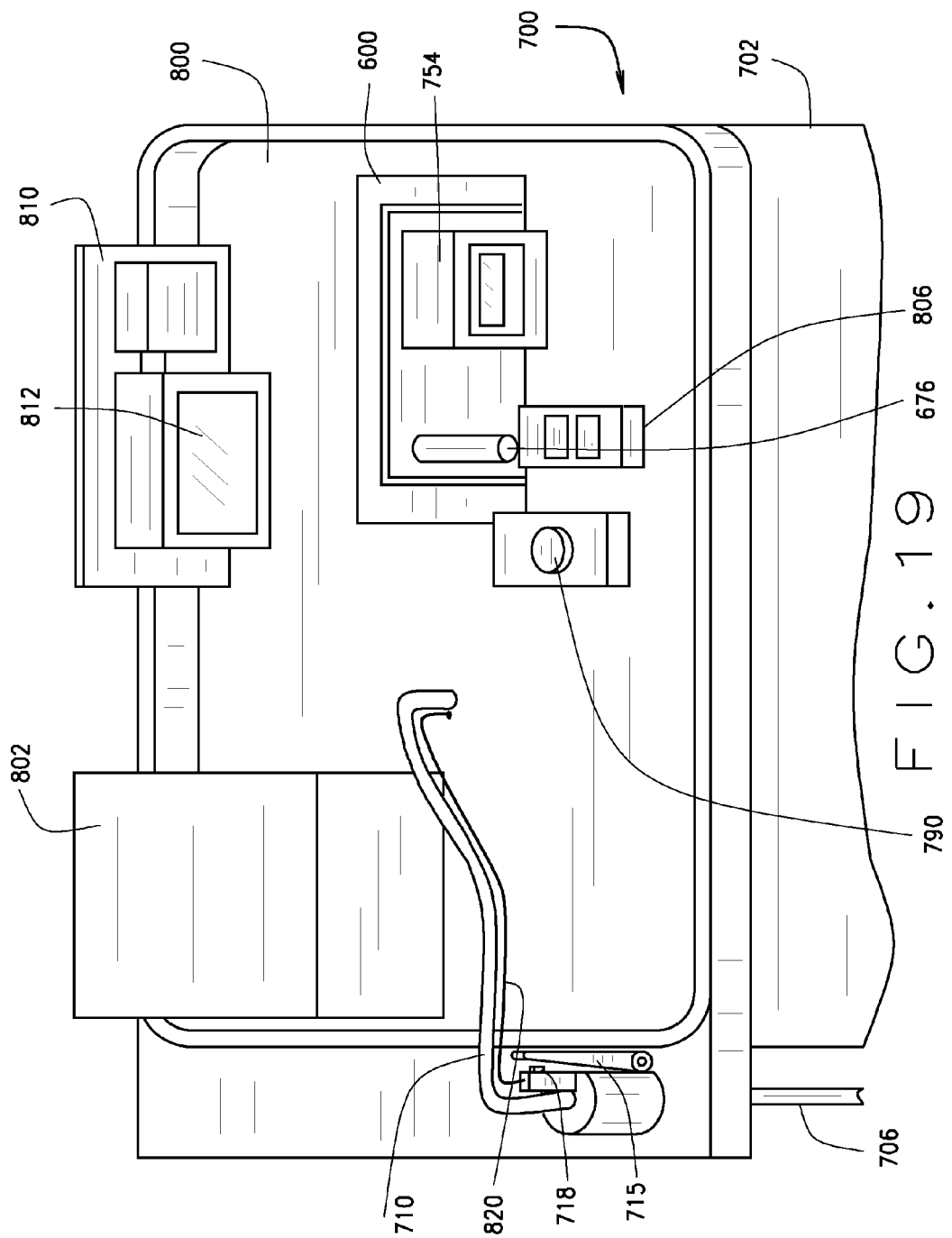
FIG. 19 is a top-down view of the second mobile system.
Figure 20:
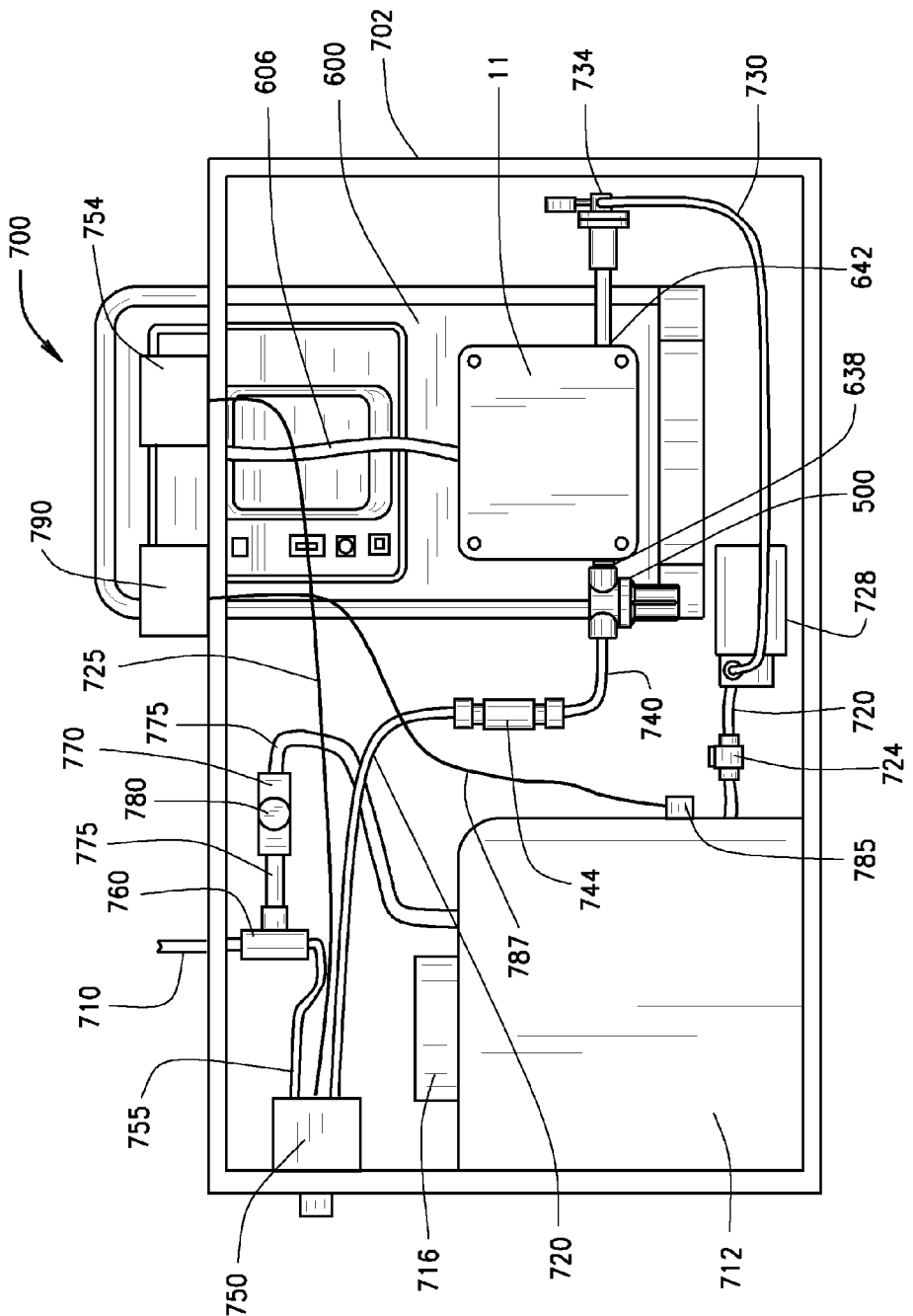
FIG. 20 is an internal view of the second mobile system.

A top surface 800 of the second mobile system 700 is shown in FIG. 19. A power supply 802 provides power to the oxygen concentrator 600, the pump 728 and the ozonated liquid dispensing unit 11, and the other electrical components of the second mobile system 700. The power supply 802 includes a battery, such as a 12V battery, that may be charged by plugging into a source of alternating current. Inverters and other charging apparatus may be used in conjunction with the power supply 802 to provide for the recharging for the battery. The system 700 may also be plugged directly into a source of alternating current and operate from the alternating current without using the battery.

The wand 706 includes a handle 715. When the operator squeezes the handle 715, the ozonated fluid is permitted to flow through the wand 706 and a switch 718 is tripped or activated by the handle 715. Activation of the switch 718 activates the pump 728 to begin pumping fluid from the tank 712 via the fluid line 730 to the ozonated liquid dispensing unit 11. Activation of the switch 718 further initiates the oxygen concentrator 600 to begin producing oxygen gas for the ozonated liquid dispensing unit 11. When the fluid reaches the ozonated liquid dispensing unit 11 via the fluid line 730, the flow switch 648 activates the first and second dielectric cells 602 and 612. The switch 718 may include a microswitch that triggers when the handle 715 is squeezed.

The second mobile system 700 may include a time delay circuit. The time delay circuit sets the amount of time the pump 728 and the oxygen concentrator 600 are kept on after the switch 718 is released. The time delay circuit may also be adjustable.

An ambient ozone monitor 810 measures ozone gas from the surrounding environment. The levels of ozone gas in the ambient air, as measured by the ambient ozone monitor 810 are displayed on a display 812. The ambient ozone monitor 810 may also shut the system 700 down if the ambient ozone gas levels exceed certain levels.

The system 700 may be used to clean and sanitize by spraying the mist of ozonated fluid onto articles and/or surfaces. No wiping or mopping is required. As such, labor for cleaning is significantly reduced. Further, the use of the system 700 often achieves better results than using conventional methods for cleaning, Those skilled in the art will appreciate that variations from the specific embodiments disclosed above are contemplated by the invention. The invention should not be restricted to the above embodiments, but should be measured by the following claims.

What is claimed:

1. A mobile system for producing an ozonated liquid, comprising:
   an ozonated liquid dispensing unit to form ozone gas and to form an ozonated liquid;
   the ozonated liquid dispensing unit including a liquid input port for connecting to a supply of water, the ozonated liquid dispensing unit including an ozone gas generator to generate the ozone gas, and the ozonated liquid dispensing unit forms the ozonated liquid from water from the supply of water and from the ozone gas from the ozone generator; and,
   a reaction vessel fluidly connected to the ozonated liquid dispensing unit, wherein the reaction vessel comprises a container and a core, and the ozonated liquid from the ozonated liquid dispensing unit passes through the reaction vessel, wherein the core includes a solid structure, and the reaction vessel reduces bubble size of the ozone gas in the ozonated liquid.

2. The mobile system according to claim 1, wherein the mobile system connects to a source of electricity and to the supply of water, wherein the water is directed to the liquid input port, and the ozonated liquid is dispensed from a fluid exit opening.

3. The mobile system according to claim 1, wherein the container comprises walls, and the walls position the core.

4. The mobile system according to claim 1, wherein the container defines an open volume, and the container contains the core in the open volume.

5. The mobile system according to claim 1, wherein the ozonated fluid enters the container, the ozonated fluid is processed about the core, and the ozonated fluid exits the container from a fluid exit opening.

6. The mobile system according to claim 5, wherein the fluid exit opening is in fluidic communication with an applicator via a fluid line.

7. The mobile system according to claim 1, wherein the container includes container walls that surround the core, an annulus is formed by an open volume between the container walls and the core, and the ozonated liquid circulates in the annulus about the core.

8. The mobile system according to claim 1, wherein the core includes a cone-shaped structure.

9. The mobile system according to claim 1, wherein the core includes a cone-shaped structure comprising a ridged surface.

10. The mobile system according to claim 1, wherein the core includes a cone-shaped structure comprising a ridged surface with 5 to 30 ridges.

11. The mobile system according to claim 1, wherein the ozonated liquid passes through an annular gap between a surface of a wider portion of the core and a container wall.

12. A mobile system for producing an ozonated liquid, comprising:
an ozonated liquid dispensing unit to form ozone gas and inject the ozone gas into water,
the ozonated liquid dispensing unit including a liquid input port for connecting to a supply of the water, the ozonated liquid dispensing unit including an ozone gas generator to generate the ozone gas, and the ozonated liquid dispensing unit forms an ozonated liquid from the water from the supply of water and from the ozone gas from the ozone gas generator; and,
a reaction vessel fluidly connected to the ozonated liquid dispensing unit, wherein the reaction vessel comprises a container and a core, wherein the core includes a cone-shaped structure, and the ozonated liquid from the ozonated liquid dispensing unit passes through the reaction vessel, wherein the container includes container walls that surround the core, an annulus is formed by an open volume between the container walls and the core, and the ozonated liquid passes through the annulus.

13. A mobile system for dispensing an ozonated liquid, comprising:
an ozonated liquid dispensing unit comprising an ozone gas generator;
the ozonated liquid dispensing unit including a liquid input port for connecting to a supply of water, the ozonated liquid dispensing unit including the ozone gas generator to generate ozone gas, the ozonated liquid dispensing unit comprising an injector in supply communication with the ozone generator, and the ozonated liquid dispensing unit forms an ozonated liquid by injecting the ozone gas from the ozone gas generator into the water from the supply of water;
a reaction vessel fluidly connected to the ozonated liquid dispensing unit, wherein the reaction vessel comprises a container and a core, the ozonated liquid from the ozonated liquid dispensing unit passes through the reaction vessel, the core includes a solid, cone-shaped structure, and the reaction vessel directs the ozonated liquid against the core to reduce a bubble size of the ozone gas in the ozonated liquid; and,
a liquid output port in fluidic communicate with the reaction vessel to dispense the ozonated liquid from the mobile system.

14. The mobile system according to claim 13, wherein the core includes a ridged surface.

15. The mobile system according to claim 13, wherein the ozonated liquid passes through an annular gap between a surface of a wider portion of the core and a container wall.

16. The mobile system according to claim 13, wherein the container includes container walls that surround the core, an annulus is formed by an open volume between the container walls and the core, and the ozonated liquid passes through the annulus.

17. The mobile system according to claim 13, further comprising an applicator, sprayer, fluid supply line, or distribution assembly in fluidic communication with the liquid output port to dispense the ozonated liquid from the mobile system.

18. A mobile system for producing an ozonated fluid, comprising:
an oxygen concentrator;
a reservoir of water;
an ozonated liquid dispensing unit connected to the oxygen concentrator to receive oxygen gas, and the ozonated liquid dispensing unit connected to the reservoir of water;
a reaction vessel fluidly connected to the ozonated liquid dispensing unit to receive the ozonated fluid from the ozonated liquid dispensing unit, wherein the reaction vessel processes the ozonated fluid; and,
an applicator in fluidic communication with the reaction vessel, wherein the applicator includes a handle that trips or activates a switch, and the switch activates the oxygen concentrator and a pump that directs water from the reservoir to the ozonated liquid dispensing unit.

19. A mobile system for producing an ozonated fluid, comprising:
an oxygen concentrator;
a reservoir of water;
an ozonated liquid dispensing unit connected to the oxygen concentrator to receive oxygen gas, and the ozonated liquid dispensing unit connected to the reservoir of water;
a reaction vessel fluidly connected to the ozonated liquid dispensing unit to receive the ozonated fluid from the ozonated liquid dispensing unit, wherein the reaction vessel comprises a container having container walls and a core, wherein the core includes a cone-shaped structure, and the ozonated fluid from the ozonated liquid dispensing unit passes through the reaction vessel; an annulus is formed by an open volume between the container walls and the core, and the ozonated liquid passes through the annulus, wherein the reaction vessel processes the ozonated fluid; and the reaction vessel reduces bubble size of ozone gas in the ozonated fluid; and, an applicator in fluidic communication with the reaction vessel.

20. The mobile system according to claim 19, wherein a regulator reduces back pressure on the applicator, wherein the regulator adjusts the flow of the ozonated fluid to the applicator and to the reservoir.

21. The mobile system according to claim 20, wherein the regulator is in a return fluid line, and the return fluid line returns the ozonated fluid to the reservoir, and the regulator is adjustable.

22. The mobile system according to claim 19, wherein a regulator diverts the ozonated fluid back to the reservoir.

23. The mobile system according to claim 19, wherein the reservoir of water comprises a low level sensor that signals a low water level in the reservoir of water.

24. The mobile system according to claim 19, wherein the applicator is in fluidic communication with the reaction vessel via a fluid line, and the applicator sprays a mist of the ozonated fluid.

25. The mobile system according to claim 19, further comprising a pump to transfer water from the reservoir of water to the ozonated liquid dispensing unit, and wherein the applicator activates the pump.

26. A mobile system for producing an ozonated fluid, comprising:
   an oxygen concentrator;
   a tank of a liquid;
   an ozonated liquid dispensing unit connected to the oxygen concentrator to receive oxygen gas;
   the ozonated liquid dispensing unit further connected to the tank of the liquid to receive the liquid, and wherein the ozonated liquid dispensing unit generates ozone gas from the oxygen gas and injects the ozone gas into the liquid from the tank to form the ozonated fluid;
   a reaction vessel fluidly connected to the ozonated liquid dispensing unit to process the ozonated fluid, wherein the reaction vessel comprises a container with container walls and a core, wherein the core includes a solid structure, and the ozonated fluid from the ozonated liquid dispensing unit passes through the reaction vessel, an annulus is formed by an open volume between the container walls and the core, and the ozonated liquid passes through the annulus, and the reaction vessel reduces bubble size of the ozone gas in the ozonated fluid;
   the reaction vessel in fluidic communication with a regulator; and,
   an applicator connected with the regulator to receive the ozonated fluid.

27. The mobile system according to claim 26, wherein the regulator adjusts flow of the ozonated fluid between the applicator and a return fluid line to the tank.

* * * * *